US011020054B2

(12) United States Patent
Pritchard et al.

(10) Patent No.: US 11,020,054 B2
(45) Date of Patent: Jun. 1, 2021

(54) DIAGNOSTIC AND THERAPEUTIC SPLINTS

(71) Applicant: The Florida State University Research Foundation, Inc., Tallahassee, FL (US)

(72) Inventors: Emily Pritchard, Tallahassee, FL (US); Mina-Michael Barsoum, Tallahassee, FL (US); Judy Delp, Tallahassee, FL (US); Josh Maraj, Tallahassee, FL (US); Kazuki Hotta, Niigata (JP)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 216 days.

(21) Appl. No.: 16/192,423

(22) Filed: Nov. 15, 2018

(65) Prior Publication Data

US 2019/0159728 A1  May 30, 2019

Related U.S. Application Data

(60) Provisional application No. 62/586,490, filed on Nov. 15, 2017.

(51) Int. Cl.
*A61B 5/00* (2006.01)
*A61F 5/01* (2006.01)
(Continued)

(52) U.S. Cl.
CPC ........ *A61B 5/6812* (2013.01); *A61B 5/02055* (2013.01); *A61B 5/0295* (2013.01);
(Continued)

(58) Field of Classification Search
CPC ........... A61B 5/6812; A61B 8/06; A61B 8/04; A61B 5/0295; A61B 5/6829; A61B 8/4227
(Continued)

(56) References Cited

U.S. PATENT DOCUMENTS 4,502,472 A  3/1985 Pansiera
5,520,627 A  5/1996 Malewicz
(Continued)

OTHER PUBLICATIONS

Depl, et al., "Ankle Dorsiflexion Splinting Enhances Endothelial Function of Aged Leg Muscles" (GRANTOME) 2015, Retrieved from the Internet Feb. 21, 2019 URL= http://grantome.com/grant/NIH/R21-AG044858-03 Abstract.
(Continued)

*Primary Examiner* — Amanda K Hulbert
*Assistant Examiner* — Philip C Edwards
(74) *Attorney, Agent, or Firm* — Meunier Carlin & Curfman LLC

(57) ABSTRACT

Splints for diagnostic and/or therapeutic purposes are disclosed. In one aspect, the present disclosure relates to a splint system for diagnostic and/or therapeutic functions for a patient with a vascular impairment. In one embodiment, the splint system includes a splint having: a leg supporting portion and a foot supporting portion, that are configured to support and secure the leg and foot of the patient; a locally and/or remotely controllable portion for setting a dorsiflexion angle of the foot of the patient, including electrical and/or mechanical controls and one or more actuators for setting of the dorsiflexion angle, for providing treatment to improve vascular function; and a plurality of physiological parameter sensors for measuring physiological parameters of the leg and/or foot of the patient, wherein the physiological parameters are associated with vascular function in the leg and/or foot of the patient.

25 Claims, 18 Drawing Sheets

(51) Int. Cl.
A61H 1/02 (2006.01)
A61B 5/0205 (2006.01)
A61B 7/04 (2006.01)
A61B 8/08 (2006.01)
A61B 5/1455 (2006.01)
A61B 8/06 (2006.01)
A61B 8/00 (2006.01)
A61B 8/04 (2006.01)
A61B 5/0295 (2006.01)
A61B 5/103 (2006.01)
A61B 5/022 (2006.01)
A61B 5/024 (2006.01)
A61B 5/026 (2006.01)
A61B 5/107 (2006.01)
A61F 5/058 (2006.01)
A61B 8/02 (2006.01)

(52) U.S. Cl.
CPC ........ *A61B 5/14552* (2013.01); *A61B 5/4836* (2013.01); *A61B 5/6829* (2013.01); *A61B 7/04* (2013.01); *A61B 8/04* (2013.01); *A61B 8/06* (2013.01); *A61B 8/4209* (2013.01); *A61B 8/4227* (2013.01); *A61B 8/4427* (2013.01); *A61B 8/488* (2013.01); *A61F 5/0127* (2013.01); *A61H 1/0266* (2013.01); *A61B 5/026* (2013.01); *A61B 5/02233* (2013.01); *A61B 5/02416* (2013.01); *A61B 5/1036* (2013.01); *A61B 5/1071* (2013.01); *A61B 8/02* (2013.01); *A61B 8/461* (2013.01); *A61B 8/5223* (2013.01); *A61F 5/0585* (2013.01); *A61F 2005/0155* (2013.01); *A61F 2005/0167* (2013.01); *A61H 2201/0173* (2013.01); *A61H 2201/0192* (2013.01); *A61H 2201/1215* (2013.01); *A61H 2201/165* (2013.01); *A61H 2201/1642* (2013.01); *A61H 2201/5007* (2013.01); *A61H 2201/5025* (2013.01); *A61H 2201/5069* (2013.01); *A61H 2201/5097* (2013.01); *A61H 2205/106* (2013.01); *A61H 2209/00* (2013.01); *A61H 2230/00* (2013.01); *A61H 2230/207* (2013.01); *A61H 2230/30* (2013.01); *A61H 2230/50* (2013.01)

(58) Field of Classification Search
USPC .......................................................... 600/301
See application file for complete search history.

(56) References Cited

U.S. PATENT DOCUMENTS

| | | | |
|---|---|---|---|
| 6,010,468 | A | 1/2000 | Grove et al. |
| 6,170,175 | B1 | 1/2001 | Funk |
| 6,409,695 | B1 | 6/2002 | Connelly |
| 6,666,796 | B1 | 12/2003 | MacCready, Jr. |
| 9,398,970 | B1 | 7/2016 | Meyer |
| 2010/0280629 | A1* | 11/2010 | Jung .......................... A61F 2/66 623/53 |
| 2013/0144140 | A1* | 6/2013 | Frederick ............. A61B 5/0075 600/324 |
| 2016/0361189 | A1 | 12/2016 | Becker |
| 2017/0100300 | A1 | 4/2017 | Rapp et al. |
| 2017/0296139 | A1* | 10/2017 | Giaya ..................... A61B 8/463 |

OTHER PUBLICATIONS

Aboyans V, et al., Measurement and interpretation of the ankle-brachial index: a scientific statement from the American Heart Association. Circulation. 2012;126:2890-909.

Ades PA, et al., Skeletal muscle and cardiovascular adaptations to exercise conditioning in older coronary patients. Circulation 94: 323-330, 1996.

Agata N, et al., Repetitive stretch suppresses denervation-induced atrophy of soleus muscle in rats. Muscle Nerve 39: 456-462, 2009.

Aliev MK, and Saks VA. Quantitative analysis of the 'phosphocreatine shuttle': I. A probability approach to the description of phosphocreatine production in the coupled creatine kinase-ATP/ADP translocase-oxidative phosphorylation reactions in heart mitochondria. Biochim Biophys Acta 1143: 291-300, 1993.

Allison MA, Ho E, Denenberg JO, Langer RD, Newman AB, Fabsitz RR and Criqui MH. Ethnic-specific prevalence of peripheral arterial disease in the United States. Am J Prev Med. 2007;32:328-33.

Alsop DC, et al., Recommended implementation of arterial spin-labeled perfusion MRI for clinical applications: A consensus of the ISMRM perfusion study group and the European consortium for ASL in dementia. Magn Reson Med 73: 102-116, 2015.

Anderson JL, et la., Management of patients with peripheral artery disease (compilation of 2005 and 2011 ACCF/AHA guideline recommendations): a report of the American College of Cardiology Foundation/American Heart Association Task Force on Practice Guidelines. Circulation. 2013, 16 pages.

Behnke BJ, et al., Effects of aging and exercise training on skeletal muscle blood flow and resistance artery morphology. J Appl Physiol (1985) 113: 1699-1708, 2012.

Behringer EJ and Segal SS. Spreading the signal for vasodilatation: implications for skeletal muscle blood flow control and the effects of ageing. J Physiol. 2012;590:6277-84.

Bendahan D, Chatel B, and Jue T. Comparative NMR and NIRS analysis of oxygen-dependent metabolism in exercising finger flexor muscles. Am J Physiol Regul Integr Comp Physiol 313: R740-R753, 2017.

Benjamin EJ, et al., Heart Disease and Stroke Statistics—2018 Update: A Report from the American Heart Association. Circulation 137: e67-e492, 2018.

Brendle DC, Joseph LJO, Corretti MC, Gardner AW and Katzel LI. Effects of exercise rehabilitation on endothelial reactivity in older patients with peripheral arterial disease. Am J Cardiol. 2001;87:324-329.

Candow DG, Chilibeck PD, and Forbes SC. Creatine supplementation and aging musculoskeletal health. Endocrine 45: 354-361, 2014.

Candow DG, Little JP, Chilibeck PD, Abeysekara S, Zello GA, Kazachkov M, Cornish SM, and Yu PH. Low-dose creatine combined with protein during resistance training in older men. Med Sci Sports Exerc 40: 1645-1652, 2008.

Cartee GD. Aging skeletal muscle: response to exercise. Exerc Sport Sci Rev 22: 91-120, 1994.

Chen C, Stephenson MC, Peters A, Morris PG, Francis ST, and Gowland PA. (31) P magnetization transfer magnetic resonance spectroscopy: Assessing the activation induced change in cerebral ATP metabolic rates at 3 T. Magn Reson Med 79: 22-30, 2018.

Chen HC, Patel V, Wiek J, Rassam SM and Kohner EM. Vessel diameter changes during the cardiac cycle. Eye (Lond). 1994;8 ( Pt 1):97-103.

Cook SB, LaRoche DP, Villa MR, Barile H, and Manini TM. Blood flow restricted resistance training in older adults at risk of mobility limitations. Exp Gerontol 99: 138-145, 2017.

Cress ME, Buchner DM, Questad KA, Esselman PC, deLateur BJ, and Schwartz RS. Continuousscale physical functional performance in healthy older adults: a validation study. Arch Phys Med Rehabil 77:1243-1250, 1996.

Delpy DT, and Cope M. Quantification in tissue near-infrared spectroscopy. Philosophical Transactions of the Royal Society B: Biological Sciences 352: 649-659, 1997.

Devries MC, and Phillips SM. Creatine supplementation during resistance training in older adults-ameta-analysis. Med Sci Sports Exerc 46: 1194-1203, 2014.

Dorsi Free Streach—531, accessed on-line: https://www.orthomerica.com/pdf/orthometry/tcflex/tcf_of_dorsifree_stretch.pdf Nov. 11, 2018, 2 pages.

(56) References Cited

OTHER PUBLICATIONS

Duke J, Chase M, Poznanski-Ring N, Martin J, Fuhr R, and Chatterjee A. Natural Language Processing to Improve Identification of Peripheral Arterial Disease in Electronic Health Data. Journal of the American College of Cardiology 67: 2280, 2016.

Esterhammer R, Schocke M, Gorny O, Posch L, Messner H, Jaschke W, Fraedrich G, and Greiner A. Phosphocreatine kinetics in the calf muscle of patients with bilateral symptomatic peripheral arterial disease during exhaustive incremental exercise. Mol Imaging Biol 10: 30-39, 2008.

Ferrari M, and Quaresima V. A brief review on the history of human functional near-infrared spectroscopy (fNIRS) development and fields of application. NeuroImage 63: 921-935, 2012.

Ferrari M, Mottola L, and Quaresima V. Principles, techniques, and limitations of near infrared spectroscopy. Can J Appl Physiol 29: 463-487, 2004.

Gardner AW, Katzel LI, Sorkin JD, Bradham DD, Hochberg MC, Flinn WR and Goldberg AP. Exercise rehabilitation improves functional outcomes and peripheral circulation in patients with intermittent claudication: a randomized controlled trial. J Am Geriatr Soc. 2001;49:755-62.

Gardner AW, Parker DE, Montgomery PS, Scott KJ and Blevins SM. Efficacy of quantified home-based exercise and supervised exercise in patients with intermittent claudication: a randomized controlled trial. Circulation. 2011;123:491-8.

Gerhard-Herman MD, et al., 2016 AHA/ACC Guideline on the Management of Patients with Lower Extremity Peripheral Artery Disease: A Report of the American College of Cardiology/American Heart Association Task Force on Clinical Practice Guidelines. Circulation 135: e726-e779, 2017.

Greiner A, et al., High-energy phosphate metabolism during incremental calf exercise in patients with unilaterally symptomatic peripheral arterial disease measured by phosphor 31 magnetic resonance spectroscopy. Journal of Vascular Surgery 43: 978-986, 2006.

Guo Y, Logan HL, Glueck DH, and Muller KE. Selecting a sample size for studies with repeated measures. BMC Medical Research Methodology 13: 100, 2013.

Hamburg NM, and Balady GJ. Exercise rehabilitation in peripheral artery disease: functional impact and mechanisms of benefits. Circulation 123: 87-97, 2011.

Hamburg NM, and Creager MA. Pathophysiology of Intermittent Claudication in Peripheral Artery Disease. Circ J 81: 281-289, 2017.

Hellsten Y, Rufener N, Nielsen JJ, Hoier B, Krustrup P and Bangsbo J. Passive leg movement enhances interstitial VEGF protein, endothelial cell proliferation, and eNOS mRNA content in human skeletal muscle. Am J Physiol Regul Integr Comp Physiol. 2008;294:R975-82.

Hoier B, Rufener N, Bojsen-Moller J, Bangsbo J and Hellsten Y. The effect of passive movement training on angiogenic factors and capillary growth in human skeletal muscle. J Physiol. 2010;588:3833-45.

Hotta K, et al., Daily Passive Muscle Stretching Improves Flow-Mediated Dilation of Popliteal Artery and 6MWT in Elderly Patients with Stable Symptomatic Peripheral Artery Disease. International Jourrnal of Cardiology submitted: 2018. 7 pages. https://doi.org/10.1016/j.carrev.2019.05.003.

Hotta K, Behnke B, Christou D, Ghosh P, Maher P, Kurien D, Verma R and Muller-Delp J. Effects of Muscle Stretching on Endothelium-Dependent Vasodilation and Skeletal Muscle Blood Flow of Aged Rats. Circulation. 2015;130 Suppl 2:A12490.

Hotta K, Behnke B, Ghosh P, Chen B, Churchill A, Elam M, Pourafshar S, Arjmandi B, Maher P, Kurien D, Verma R, Christou D and Muller-Delp J. Effects of Muscle Stretching on Skeletal Muscle Microcirculation in Old Rats. FASEB J. 2016;30 Suppl 1:946.2.

Hotta K, Behnke BJ, Arjmandi B, Ghosh P, Chen B, Brooks R, Maraj JJ, Elam ML, Maher P, Kurien D, Churchill A, Sepulveda JL, Kabolowsky MB, Christou DD, and Muller-Delp JM. Daily muscle stretching enhances blood flow, endothelial function, capillarity, vascular vol. And connectivity in aged skeletal muscle J Physiol 596.10 (2018) pp. 1903-1917.

Huppert TJ, Hoge RD, Diamond SG, Franceschini MA, and Boas DA. A temporal comparison of BOLD, ASL, and NIRS hemodynamic responses to motor stimuli in adult humans. Neuroimage 29: 368-382, 2006.

International Search Report and Written Opinion issued for Application No. PCT/US2018/061327, dated Mar. 18, 2019, 14 pages.

Isbell DC, Berr SS, Toledano AY, Epstein FH, Meyer CH, Rogers WJ, Harthun NL, Hagspiel KD, Weltman A, and Kramer CM. Delayed calf muscle phosphocreatine recovery after exercise identifies peripheral arterial disease. J Am Coll Cardiol 47: 2289-2295, 2006.

Iwamoto A, et al., Vascular Function and Intima-media Thickness of a Leg Artery in Peripheral Artery Disease: A Comparison of Buerger Disease and Atherosclerotic Peripheral Artery Disease. J Atheroscler Thromb. 2016;23:1261-1269.

Jaff MR, Dale RA, Creager MA, Lipicky RJ, Constant J, Campbell LA and Hiatt WR. Anti-chlamydial antibiotic therapy for symptom improvement in peripheral artery disease: prospective evaluation of rifalazil effect on vascular symptoms of intermittent claudication and other endpoints in Chlamydia pneumoniae seropositive patients (PROVIDENCE-1). Circulation. 2009;119:452-8.

Laboratories ATSCoPSfCPF. ATS statement: guidelines for the six-minute walk test. Am J Respir Crit Care Med. 2002;166:111-7.

Li X, Wang D, Auerbach EJ, Moeller S, Ugurbil K, and Metzger GJ. Theoretical and experimental evaluation of multi-band EPI for high-resolution whole brain pCASL Imaging. Neuroimage 106: 170-181, 2015.

Lindgren H, Qvarfordt P, Akesson M, Bergman S, Gottsater A and Swedish Endovascular Claudication Stenting T. Primary Stenting of the Superficial Femoral Artery in Intermittent Claudication Improves Health Related Quality of Life, ABI and Walking Distance: 12 Month Results of a Controlled Randomised Multicentre Trial. Eur J Vasc Endovasc Surg. 2017;53:686-694.

Long J, Modrall JG, Parker BJ, Swann A, Welborn MB and Anthony T. Correlation between ankle-brachial index, symptoms, and health-related quality of life in patients with peripheral vascular disease. Journal of Vascular Surgery. 2004; 39:723-727.

Lott DJ, Forbes SC, Mathur S, Germain SA, Senesac CR, Lee Sweeney H, Walter GA, and Vandenborne K. Assessment of intramuscular lipid and metabolites of the lower leg using magnetic resonance spectroscopy in boys with Duchenne muscular dystrophy. Neuromuscul Disord 24: 574-582, 2014.

Luck JC, Miller AJ, Aziz F, Radtka JF, 3rd, Proctor DN, Leuenberger UA, Sinoway LI and Muller MD. Blood pressure and calf muscle oxygen extraction during plantar flexion exercise in peripheral artery disease. J Appl Physiol (1985). 2017;123:2-10.

Makris KI, Nella AA, Zhu Z, Swanson SA, Casale GP, Gutti TL, Judge AR, and Pipinos, II. Mitochondriopathy of peripheral arterial disease. Vascular 15: 336-343, 2007.

McDermott MM, Ades PA, Dyer A, Guralnik JM, Kibbe M and Criqui MH. Corridor-based functional performance measures correlate better with physical activity during daily life than treadmill measures in persons with peripheral arterial disease. J Vasc Surg. 2008;48:1231-1237 e1.

McDermott MM, Ferrucci L, Simonsick EM, Balfour J, Fried L, Ling S, Gibson D, and GuralnikJM. The ankle brachial index and change in lower extremity functioning over time: the Women's Health and Aging Study. J Am Geriatr Soc 50: 238-246, 2002.

McDermott MM, Greenland P, Liu K, Guralnik JM, Celic L, Criqui MH, Chan C, Martin GJ, Schneider J, Pearce WH, Taylor LM and Clark E. The ankle brachial index is associated with leg function and physical activity: The walking and leg circulation study. Ann Intern Med. 2002;136:873-883.

McDermott MM, Greenland P, Liu K, Guralnik JM, Criqui MH, Dolan NC, Chan C, Celic L, Pearce WH, Schneider JR, Sharma L, Clark E, Gibson D and Martin GJ. Leg symptoms in peripheral arterial disease: associated clinical characteristics and functional impairment. JAMA. 2001;286:1599-606.

McDermott MM, Guralnik JM, Criqui MH, Ferrucci L, Liu K, Spring B, Tian L, Domanchuk K, Kibbe M, Zhao L, Lloyd Jones D,

(56) References Cited

OTHER PUBLICATIONS

Liao Y, Gao Y and Rejeski WJ. Unsupervised exercise and mobility loss in peripheral artery disease: a randomized controlled trial. J Am Heart Assoc. 2015;4, 13 pages.

McDermott MM, Guralnik JM, Criqui MH, Liu K, Kibbe MR and Ferrucci L. Six-Minute Walk Is a Better Outcome Measure Than Treadmill Walking Tests in Therapeutic Trials of Patients with Peripheral Artery Disease. Circulation. 2014;130:61-68.

McDermott MM, Guralnik JM, Tian L, Ferrucci L, Liu K, Liao Y and Criqui MH. Baseline functional performance predicts the rate of mobility loss in persons with peripheral arterial disease. J Am Coll Cardiol. 2007;50:974-82.

McDermott MM, Liu K, Ferrucci L, Tian L, Guralnik JM, Liao Y and Criqui MH. Decline in functional performance predicts later increased mobility loss and mortality in peripheral arterial disease. J Am Coll Cardiol. 2011;57:962-70.

McDermott MM, Liu K, Greenland P, Guralnik JM, Criqui MH, Chan C, Pearce WH, Schneider JR, Ferrucci L, Celic L, Taylor LM, Vonesh E, Martin GJ and Clark E. Functional decline in peripheral arterial disease: associations with the ankle brachial index and leg symptoms. JAMA. 2004;292:453-61.

McDermott MM. Lower extremity manifestations of peripheral artery disease: the pathophysiologic and functional implications of leg ischemia. Circ Res 116: 1540-1550, 2015.

Montgomery PS and Gardner AW. The clinical utility of a six-minute walk test in peripheral arterial occlusive disease patients. J Am Geriatr Soc. 1998;46:706-11.

Motwani, Manish, et al. "Machine learning for prediction of all-cause mortality in patients with suspected coronary artery disease: a 5-year multicentre prospective registry analysis." European heart journal 38.7 (2016): 500-507.

Murphy TP, et al., Supervised exercise versus primary stenting for claudication resulting from aortoiliac peripheral artery disease: six-month outcomes from the claudication: exercise versus endoluminal revascularization (CLEVER) study. Circulation. 2012;125:130-9.

Norgren L, Hiatt WR, Dormandy JA, Nehler MR, Harris KA, Fowkes FG and Group TIW. Inter-Society Consensus for the Management of Peripheral Arterial Disease (TASC II). J Vasc Surg. 2007;45 Suppl S:S5-67.

Ordidge RJ, Connelly A, and Lohman JAB. Image-Selected Invivo Spectroscopy (Isis)—a New Technique for Spatially Selective Nmr-Spectroscopy. Journal of Magnetic Resonance 66: 283-294, 1986.

Pathare NC, Stevens JE, Walter GA, Shah P, Jayaraman A, Tillman SM, Scarborough MT, Parker Gibbs C, and Vandenborne K. Deficit in human muscle strength with cast immobilization: contribution of inorganic phosphate. Eur J Appl Physiol 98: 71-78, 2006.

Perera S, Mody SH, Woodman RC and Studenski SA. Meaningful change and responsiveness in common physical performance measures in older adults. Journal of the American Geriatrics Society. 2006;54:743-749.

Pipinos, II, Sharov VG, Shepard AD, Anagnostopoulos PV, Katsamouris A, Todor A, Filis KA, and Sabbah HN. Abnormal mitochondrial respiration in skeletal muscle in patients with peripheral arterial disease. J Vasc Surg 38: 827-832, 2003.

Poortmans JR, and Francaux M. Long-term oral creatine supplementation does not impair renal function in healthy athletes. Med Sci Sports Exerc 31: 1108-1110, 1999.

Poortmans JR, Auquier H, Renaut V, Durussel A, Saugy M, and Brisson GR. Effect of short-term creatine supplementation on renal responses in men. Eur J Appl Physiol Occup Physiol 76: 566-567, 1997.

Pyke KE and Tschakovsky ME. The relationship between shear stress and flow-mediated dilatation: implications for the assessment of endothelial function. J Physiol—London. 2005;568:357-369.

Rakobowchuk M, Tanguay S, Burgomaster KA, Howarth KR, Gibala MJ and MacDonald MJ. Sprint interval and traditional endurance training induce similar improvements in peripheral arterial stiffness and flow-mediated dilation in healthy humans. Am J Physiol Regul Integr Comp Physiol. 2008;295:R236-42.

Robbins JL, Jones WS, Duscha BD, Allen JD, Kraus WE, Regensteiner JG, Hiatt WR and Annex BH. Relationship between leg muscle capillary density and peak hyperemic blood flow with endurance capacity in peripheral artery disease. J Appl Physiol. 2011;111:81-86.

Ross EG, Shah NH, Dalman RL, Nead KT, Cooke JP, and Leeper NJ. The use of machine learning for the identification of peripheral artery disease and future mortality risk. J Vasc Surg 64: 1515-1522 e1513, 2016.

Šedivý P, Kipfelsberger MC, Dezortová M, Krššák M, Drobný M, Chmelík M, Rydlo J, Trattnig S, Hájek M, and Valkovič L. Dynamic 31P MR spectroscopy of plantar flexion: Influence of ergometer design, magnetic field strength (3 and 7 T), and RF-coil design. Medical Physics 42: 1678-1689, 2015.

Selvin E, and Erlinger TP. Prevalence of and risk factors for peripheral arterial disease in the United States: results from the National Health and Nutrition Examination Survey, 1999-2000. Circulation 110: 738-743, 2004.

Sharov VG, Saks VA, Kupriyanov VV, Lakomkin VL, Kapelko VI, Steinschneider A, and Javadov SA. Protection of ischemic myocardium by exogenous phosphocreatine. I. Morphologic and phosphorus 31-nuclear magnetic resonance studies. J Thorac Cardiovasc Surg 94: 749-761, 1987.

Solway S, Brooks D, Lacasse Y and Thomas S. A qualitative systematic overview of the measurement properties of functional walk tests used in the cardiorespiratory domain. Chest. 2001;119:256-70.

Stefan D, Di Cesare F, Andrasescu A, Popa E, Lazariev A, Vescovo E, Strbak O, Williams S, Starcuk Z, Cabanas M, van Ormondt D, and Graveron-Demilly D. Quantitation of magnetic resonance spectroscopy signals: the jMRUI software package. Meas Sci Technol 20: 2009 104035.

Tran TK, Sailasuta N, Kreutzer U, Hurd R, Chung Y, Mole P, Kuno S, and Jue T. Comparative analysis of NMR and NIRS measurements of intracellular PO2 in human skeletal muscle. Am J Physiol 276: R1682-1690, 1999.

Vandenborne K, Walter G, Ploutz-Snyder L, Dudley G, Elliott MA, and De Meirleir K. Relationship between muscle T2 relaxation properties and metabolic state: a combined localized 31P-spectroscopy and 1H-imaging study. Eur J Appl Physiol 82: 76-82, 2000.

Vanhamme L, van den Boogaart A, and Van Huffel S. Improved method for accurate and efficient quantification of MRS data with use of prior knowledge. J Magn Reson 129: 35-43, 1997.

Walter G, Vandenborne K, McCully KK, and Leigh JS. Noninvasive measurement of phosphocreatine recovery kinetics in single human muscles. Am J Physiol 272: C525-534, 1997.

Wang Z, Aguirre GK, Rao H, Wang J, Fernandez-Seara MA, Childress AR, and Detre JA. Empirical optimization of ASL data analysis using an ASL data processing toolbox: ASLtbx. Magn Reson Imaging 26: 261-269, 2008.

Wang Z. Improving cerebral blood flow quantification for arterial spin labeled perfusion MRI by removing residual motion artifacts and global signal fluctuations. Magn Reson Imaging 30: 1409-1415, 2012.

Wilson RC and Jones PW. A comparison of the visual analogue scale and modified Borg scale for the measurement of dyspnoea during exercise. Clin Sci (Lond). 1989;76:277-82.

Writing Committee M, Gerhard-Herman MD, et al., 2016 AHA/ACC Guideline on the Management of Patients with Lower Extremity Peripheral Artery Disease: Executive Summary. Vasc Med 22: NP1-NP43, 2017, e686-e725.

Wu AZ, Coresh J, Selvin E, Tanaka H, Heiss G, Hirsch AT, Jaar BG and Matsushita K. Lower Extremity Peripheral Artery Disease and Quality of Life Among Older Individuals in the Community. Journal of the American Heart Association. 2017;6 e004519.

International Preliminary Report on Patentability for International Application No. PCT/US2018/061327 dated May 19, 2020.

* cited by examiner

DIAGNOSTIC AND THERAPEUTIC SPLINTS

CROSS-REFERENCE TO RELATED APPLICATIONS

This application claims the benefit of priority to 62/586,490 filed Nov. 15, 2017, the disclosure of which is incorporated herein by reference in its entirety.

STATEMENT REGARDING FEDERALLY SPONSORED RESEARCH

This invention was made with government support under Grant nos. AG055029-01A1 and AG044858-03 awarded by the National Institutes of Health. The government has certain rights in the invention.

BACKGROUND

Patients with peripheral arterial disease (PAD) often have walking impairment and pain during walking (claudication) due to insufficient oxygen supply to leg muscles. Existing clinical treatment of PAD involves walking programs or revascularization. Surgery can carry significant costs and risks of acute complications from, for instance, recurrences due to restenosis or graft occlusion. Adherence to long-term walking programs can be difficult for frail patients such as the elderly. It is with respect to these and other considerations that the various embodiments described below are presented.

SUMMARY

In some aspects, the present disclosure relates to diagnostics and treatment associated with vascular impairments, and particularly peripheral arterial disease (PAD). As mentioned above, patients with PAD often have walking impairment and pain during walking due to insufficient oxygen supply to leg muscles. Stretching of calf muscles improves vascular function in the lower leg. Use of a splint such as one or more of the splint embodiments disclosed herein can enhance a patient's vascular function, for example improving blood flow in the leg, and decrease pain during normal gait.

According to a first aspect of the disclosure, a splint for a diagnostic test and/or therapeutic treatment of patients with a vascular impairment comprises a leg support surface that defines a first cavity adapted to receive a lower leg of a patient. The splint also comprises a foot support surface adapted to receive a portion of a foot of the patient, the foot support surface coupled to the leg support surface. The splint also comprises a hinge coupled to the foot support surface to facilitate rotation of the foot support surface relative to the leg support surface between a first configuration and a second configuration. The first configuration of the hinge comprises the foot support surface at a first angle to the leg support surface. The second configuration of the hinge comprises the foot support surface at a second angle to the leg support surface, wherein the second angle is less than the first angle. The splint also comprises a mechanical stop adapted to prevent rotation of the foot support surface relative to the leg support surface to an angle less than the second angle.

In some implementations of the first aspect of the disclosure, the first angle is in a range between 80-100°.

In some implementations of the first aspect of the disclosure, the second angle is between 5-30° less than the first angle.

In some implementations of the first aspect of the disclosure, the foot support surface defines a second cavity adapted to receive the foot of the patient.

In some implementations of the first aspect of the disclosure, the foot support surface defines a heel cup adapted to support a heel of the foot of the patient.

In some implementations of the first aspect of the disclosure, the splint further comprises a first releasable strap coupled to the leg support surface across the first cavity in a first splinted configuration adapted to restrict relative movement between the leg support surface and the lower leg of the patient. The splint further comprise a second releasable strap coupled to the foot support surface across the second cavity in a second splinted configuration adapted to restrict relative movement between the foot support surface and the foot of the patient.

In some implementations of the first aspect of the disclosure, the splint further comprises a third adjustable length strap coupled to the leg support surface at a first location and coupled to the foot support surface at a second location. A length of the third adjustable strap between the first location and the second location is less in the second configuration of the hinge than in the first configuration of the hinge.

In some implementations of the first aspect of the disclosure, the splint further comprises a fourth adjustable length strap coupled to the leg support surface at a third location opposite the first cavity from the first location and coupled to the foot support surface at a fourth location, opposite from the second location. A length of the fourth adjustable strap between the third location and the fourth location is less in the second configuration of the hinge than in the first configuration of the hinge.

In some implementations of the first aspect of the disclosure, the third adjustable length strap is one of a group of adjustable length straps consisting of: a cinch strap; a side release buckle strap; a cam buckle strap; a lashing strap; or a ratchet strap.

In some implementations of the first aspect of the disclosure, an opening for the first cavity faces towards the foot support surface.

In some implementations of the first aspect of the disclosure, an opening for the first cavity faces away from the foot support surface.

In some implementations of the first aspect of the disclosure, the mechanical stop is configured to set the second angle to induce local ischemia in a plantar flexor muscle of the lower leg of the patient.

In some implementations of the first aspect of the disclosure, the mechanical stop comprises an elongated bar with a groove therethrough and comprising a fixed end and a sliding end. The fixed end is fixedly coupled to one of the leg support surface or the foot support surface, and wherein the sliding end is slidingly coupled to the other of the leg support surface or the foot support surface. The mechanical stop further comprises a pin coupled through the groove to a fixed location along the other of the leg support surface or the foot support surface and adapted to prevent the sliding end of the elongated bar from sliding past the pin.

In some implementations of the first aspect of the disclosure, the fixed location is one of a plurality of fixed locations along the other of the leg support surface or the foot support surface to which the pin is configured to be coupled.

In some implementations of the first aspect of the disclosure, the other of the leg support surface or the foot support surface comprises a groove within which the sliding end is adapted to slide along.

In some implementations of the first aspect of the disclosure, the pin comprises a flange, wherein the sliding end is slidingly coupled to the other of the leg support surface or the foot support surface via the flange.

In some implementations of the first aspect of the disclosure, the hinge comprises an articulating and/or ratcheting hinge, and wherein the mechanical stop comprises a variable stop for setting the second angle.

In some implementations of the first aspect of the disclosure, the mechanical stop comprises a threaded guide fixedly coupled to one of the leg support surface or the foot support surface. The mechanical stop further comprises a motor fixedly coupled to the other of the leg support surface or the foot support surface, the motor comprising a drive shaft. The mechanical stop further comprises a screw coupled to the motor drive shaft for rotation therewith and threadedly coupled to the threaded guide.

In some implementations of the first aspect of the disclosure, the splint further comprises a motor driver coupled to the motor and configured to supply power to the motor for rotation of the drive shaft.

In some implementations of the first aspect of the disclosure, the splint further comprises a remote control wired or wirelessly coupled to the motor driver and configured to supply an instruction to initiate rotation of the drive shaft.

In some implementations of the first aspect of the disclosure, the splint further comprises a battery coupled to the motor driver for supplying power to the motor driver and the motor.

In some implementations of the first aspect of the disclosure, the splint further comprises a near-infrared spectroscopy oxygenation sensor.

According to a second aspect of the disclosure, a splint system for diagnostic and/or therapeutic functions for a patient with a vascular impairment comprises a splint. The splint comprises a leg supporting portion and a foot supporting portion, that are configured to support and secure the leg and foot of the patient. The splint comprises a locally and/or remotely controllable portion for setting a dorsiflexion angle of the foot of the patient, including electrical and/or mechanical controls and one or more actuators for setting of the dorsiflexion angle, for providing treatment to improve vascular function. The splint comprises a plurality of physiological parameter sensors for measuring physiological parameters of the leg and/or foot of the patient, wherein the physiological parameters are associated with vascular function in the leg and/or foot of the patient.

In some implementations of the second aspect of the disclosure, the vascular impairment is peripheral arterial disease (PAD).

In some implementations of the second aspect of the disclosure, the treatment to improve the vascular function comprises improving blood flow and/or oxygenation.

In some implementations of the second aspect of the disclosure, setting a dorsiflexion angle of the foot of the patient comprises holding the foot at a predetermined dorsiflexion angle using a plate that is located at the foot supporting portion of the splint and is operatively coupled to the one or more actuators.

In some implementations of the second aspect of the disclosure, the leg supporting portion extends behind the knee of the patient to prevent bending of the knee during use of the splint.

In some implementations of the second aspect of the disclosure, the sensors comprise one or more sensors for measuring tension applied by the splint to the leg and/or foot.

In some implementations of the second aspect of the disclosure, the splint further comprises one or more components for preventing the tension applied by the splint to reach or exceed a level associated with a clinically undesirable result.

In some implementations of the second aspect of the disclosure, the physiological parameters comprise one or more of: oxygen saturation; pulse; blood pressure; ankle-brachial index; pulse wave velocity; femoral bruit; skin temperature; or blood flow velocity.

In some implementations of the second aspect of the disclosure, the sensors comprise one or more of: at least one blood pressure cuff; at least one bruit sensor; at least one dorsiflexion angle sensor; at least one near infrared spectroscopy contact point; at least one doppler ultrasound device or tonometer; at least one photoplethysmogram; at least one tensiometer; at least one plantar pressure measurement sensor; at least one dorsalis pedis sensor; or at least one skin temperature sensor.

In some implementations of the second aspect of the disclosure, the system further comprises one or more sensors disposed separately from the splint, and wherein the sensors of the splint and/or the one or more sensors disposed separately comprise at least one of: a brachial cuff; an ankle cuff; or a blood pressure cuff integrated with the splint.

In some implementations of the second aspect of the disclosure, the system further comprises one or more computing devices coupled via wired and/or wireless connections to the splint, configured for displaying visual representations of the measured physiological parameters and/or entry of data associated with the measured physiological parameters.

In some implementations of the second aspect of the disclosure, the system further comprises a remote control device configured to remotely control the dorsiflexion angle.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIGS. 1A and 1B are partial, front isometric view and FIG. 1C is a side view.

DETAILED DESCRIPTION

Figure 1A:
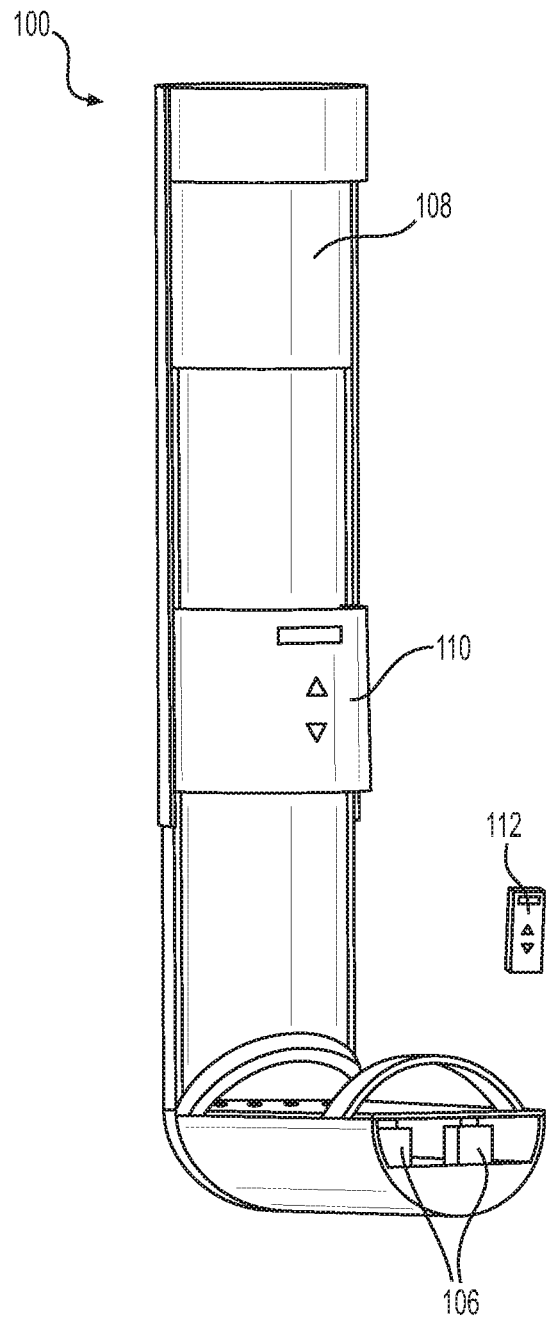
FIGS. 1A-1C schematically illustrate a splint according to one embodiment of the present disclosure, where

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" or "patient" refers to a living organism, such as a human or animal, with vascular function to be diagnosed and/or treated through the use of splints and/or splint systems described herein in accordance with various embodiments.

The following description provides a further discussion of certain aspects of the present disclosure in accordance with example embodiments. The discussion of some example implementations may also refer to corresponding results which may include experimental data. Experimental data which may be presented herein is intended for the purposes of illustration and should not be construed as limiting the scope of the present disclosure in any way or excluding any alternative or additional embodiments.

Lower extremity peripheral arterial disease (PAD) is associated with significant morbidity, mortality, and reduction in quality of life. Although walking exercise is currently the most effective prescription for PAD patients, many older or otherwise frail PAD patients have significantly reduced walking capacity, preventing engagement in exercise programs with a focus on walking. In contrast, muscle stretching can be performed by patients with limited walking capacity.

Acute muscle stretching by ankle dorsiflexion splinting induces local ischemia, leading to improved endothelial function, significant angiogenesis, hypertrophy, and greater muscle blood flow during exercise when performed daily for 4 weeks. In an example, PAD patients who underwent 4 weeks of daily splint-induced muscle stretching of the calf muscles experienced improved endothelial function of the popliteal artery as determined by flow-mediated dilation (FMD) of the popliteal artery and increased 6-minute walking distance, both continuous walking distance and total distance covered. These improvements led to improved outcomes in PAD patients in one or more of post-exercise ABI, endothelial function of the popliteal artery, microvascular blood flow within calf muscles, walking distance, and reduction of pain during activities of daily living in PAD patients. Therefore, splint-induced muscle stretching improves vascular function of the lower limb, leading to improved walking function. The intensity of muscle stretching is relatively light compared to aerobic exercise, so elderly or otherwise frail patients can perform muscle stretching with minimal risk of injury.

At infrared wavelengths, light penetrates tissue easily, making scattering the primary source of loss of signal rather than absorbance. These wavelengths are attenuated significantly by the chromophore hemoglobin and can therefore be used to determine the amount of hemoglobin present within the "field of view" of the sensor optodes. In some implementations, a near-infrared spectroscopy (NIRS) sensor is used to measure one or more of tissue oxygenation (oxyhemoglobin (O2Hb) and deoxyhemoglobin (HHb), and total tissue hemo(+myo)globin (tHb).

In one example, the NIRS sensor may be a MOXY MONITOR produced by Fortiori Design LLC, Hutchinson, Minn., which utilizes 4 wavelengths of light, at 680, 720, 760, and 800 nm. The NIRS sensor contains a single LED and two detectors placed 12.5 and 25.0 mm from the LED source. The NIRS sensor provides the oxygenation measurements (e.g., O2Hb, HHb, and/or tHb) using a spatial resolution approach. Thus the NIRS sensor is especially useful to examine microcirculation (capillaries, arterioles, and venules) as it is completely absorbed in vessels larger than 1 mm due to the high concentration of hemoglobin.

A NIRS sensor reliably assesses the degree of stretch that maximizes the decrease in intramuscular blood flow without causing intolerable discomfort to a patient. Specifically, the NIRS sensor assesses a degree of acute ankle dorsiflexion that leads to a maximal decrease in muscle oxygenation in each patient before beginning a prescribed stretching program. Placement of a splint to induce ankle dorsiflexion produces a significant decrease in blood flow to acutely stretched plantar flexor muscles. Specifically, intramuscular blood flow is reduced in the soleus and gastrocnemius muscles of PAD patients while undergoing static stretch induced by ankle dorsiflexion.

Through the use of a clinical splint incorporating a NIRS sensor, a prescriptive stretching program that should be applied to each individual patient during daily stretching may be established. The stretching program prescribes intensity (e.g., angle of dorsiflexion stretching), frequency, and duration of muscle stretching intervention. The angle of dorsiflexion stretching may be selected from between 5°-30° of dorsiflexion stretching. The angle of dorsiflexion may be adjusted throughout the stretching program (e.g., upon re-evaluation with the clinical splint), but for any given stretching session, the angle is a static angle to provide a static stretch induced by ankle dorsiflexion. Based on the prescribed stretching program, a therapeutic splint is configured with a mechanical stop set at the prescribed angle of dorsiflexion stretching. One or more sensors on the therapeutic splint may measure and log patient compliance parameters for one or more of the intensity, frequency, and duration of muscle stretching applied with the treatment splint.

Accordingly, two types splints are proposed for the diagnosis and treatment of peripheral arterial disease. A first type of splint is a diagnostic splint that is used within the clinic and may be used to take measurements which inform a patient-specific stretching treatment plan, which may include duration of use, frequency of use, and amount of applied stretch appropriate for the patient at the time of evaluation. Certain clinical outcomes may be measured by this splint to track patient progression and continue to maintain an appropriate and maximally beneficial treatment plan. The diagnostic or evaluative splint is used in a clinical setting for one or more measurements while at rest or when splint is worn in a dorsiflexed position, i.e. "acute measurements." The goal is to measure, directly or indirectly, the amount of stretch within the gastrocnemius or soleus when a certain dorsiflexion is applied to the foot in order to apply a safe and effective amount of stretch treatment for a given patient. Some measurements taken with or in conjunction with the diagnostic splint include near-infrared spectroscopy for measuring muscle oxygenation and total hemoglobin, photoplethysmography, pulse oximetry such as on a patient's toe on their splinted leg, and pressure. Other diagnostic measurements are contemplated by this disclosure.

The second splint type is for home-based use by the patient for the treatment of vascular disease. The treatment splint is used by the patient as prescribed by the clinician to achieve and maintain dorsiflexion during home-based daily treatment sessions (e.g. at least 5 days per week for effectiveness, or similar). This splint may be fully manual or may assist in dorsiflexion via motor assistance. It may include embedded measurement systems to monitor the clinical outcomes and/or patient compliance during treatment.

As briefly described above, stretching of calf muscles improves vascular function in the lower leg. Use of a splint such as one or more of the splint embodiments disclosed herein can enhance a patient's vascular function to treat PAD, for example improving blood flow and/or oxygenation in the leg, and decrease pain during normal gait. Splints according to some embodiments of the present disclosure can be used for clinical diagnostic purposes to determine optimal treatment parameters for the patient, such as the stretch of the lower leg. Splints according to some embodiments can hold the foot at a predetermined dorsiflexion angle and may control the angle to change over time for purposes of progressive diagnosis and/or treatment. The dorsiflexion angle can be static or dynamic throughout the range of motion of the foot. Certain embodiments can include sensing and/or measurement components for measuring physiological parameters (e.g., pulse oximetry and other vascular function-related metrics) associated with the patient condition, to assist in assessment of prescriptive approaches for treating the determined condition(s).

Splints according to some embodiments of the present disclosure include components for therapeutic purposes, applied to the foot and lower leg. Some embodiments may include automation functions and components to control and facilitate, among other aspects, higher splinting around the knee to encourage full extension of the patient's leg when the splint is being worn, the dorsiflexion angle, and/or control of resistance/tension. Local or remote control components can be utilized for local or remote electrical-mechanical control of various functions of the splint.

Figure 1B:
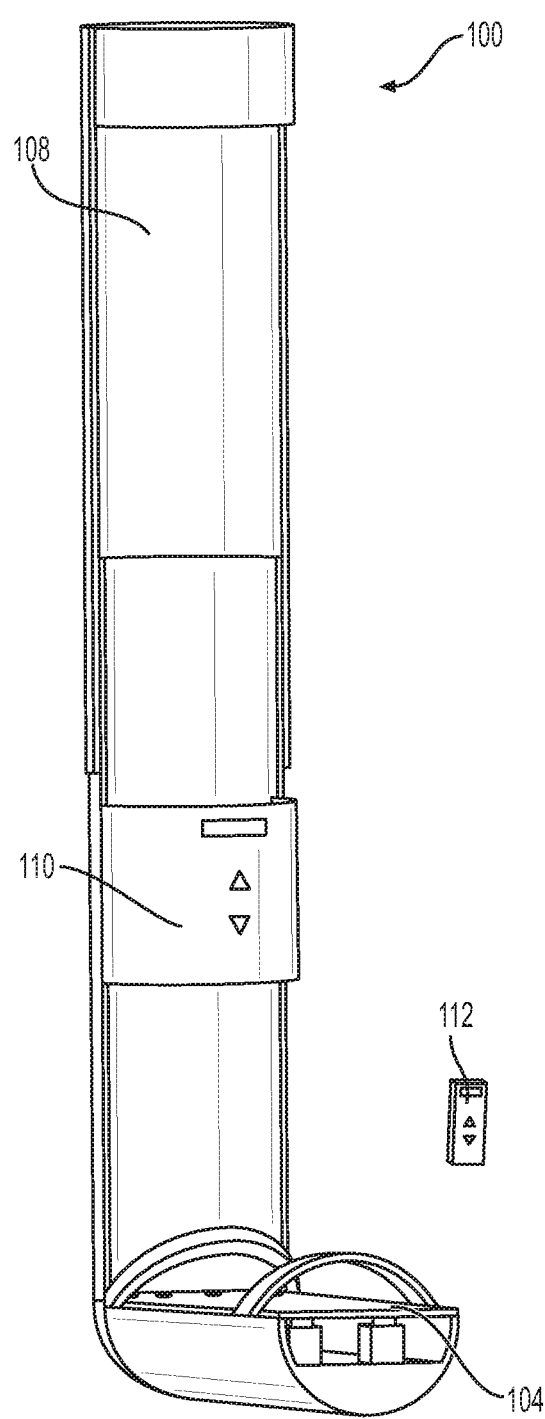
Figure 1C:
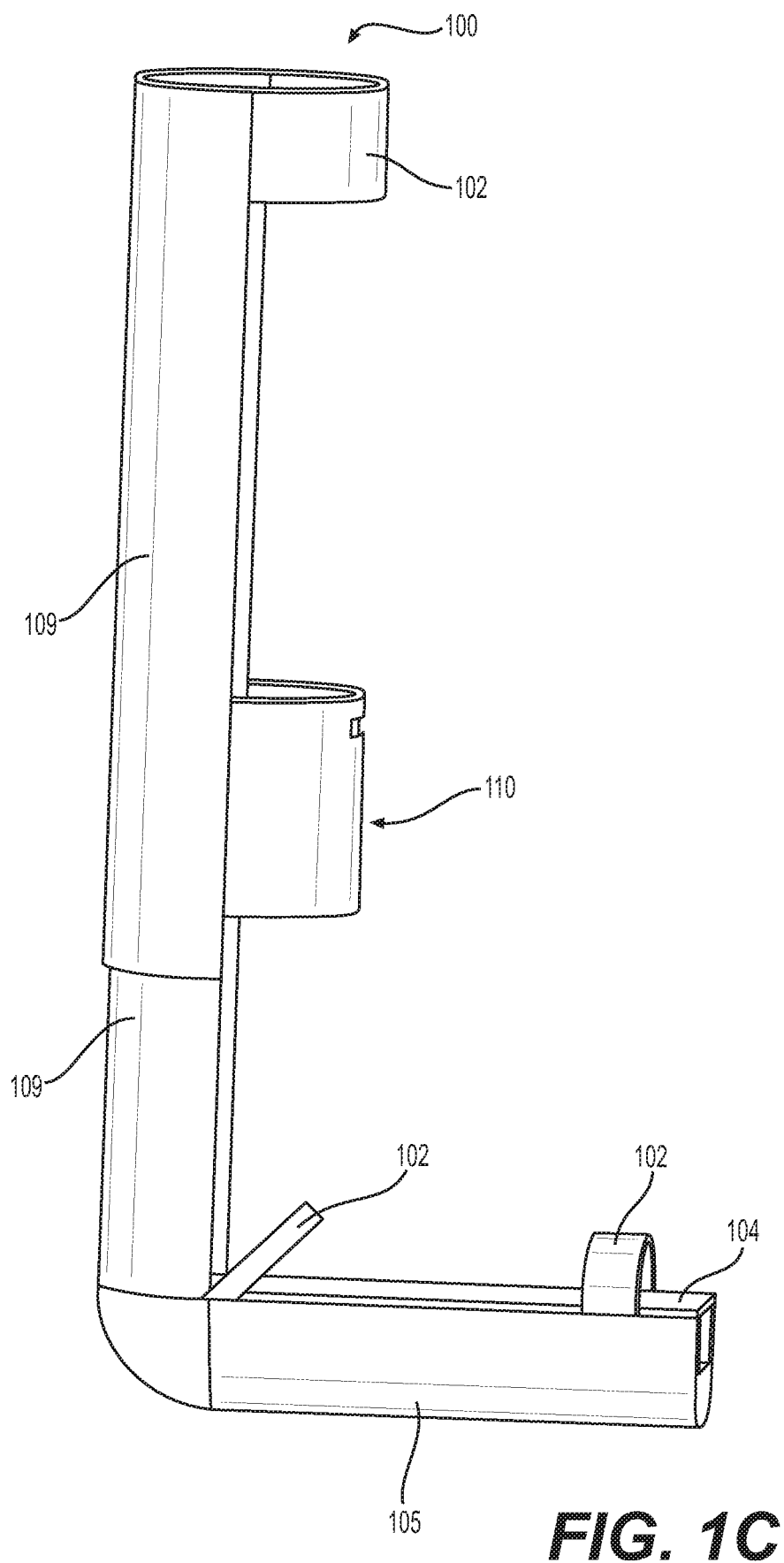

FIGS. 1A-1C schematically show a splint 100 in accordance with one embodiment of the present disclosure. The splint 100 is configured for a patient to insert his/her lower leg and foot, which are held in place by straps 102. In the example shown in FIGS. 1A-1C, the straps 102 include a shin strap, a knee strap, an ankle strap, and a foot strap to prevent relative movement between the patient's lower leg and foot with respect to the splint 100. The shin strap is positioned to securing the patient's lower leg to a leg supporting portion 109 of the splint 100 across the patient's shin. The ankle strap is positioned to secure the patient's foot against the leg supporting portion 109 of the splint 100 across the patient's ankle joint. A foot strap is positioned to secure the patient's foot to a foot supporting portion 105 of the splint 100. The knee strap is positioned at the top of the splint 100 and positioned to secure the patient's upper leg to the splint 100 across their thigh. A portion 108 of leg supporting portion 109 of the splint 100 is configured to move on rails, such that a brace portion can be extended upward behind the knee, to facilitate full extension of the leg and prevent bending of the knee when the splint 100 is in use (see change in extension of portion 108 from FIG. 1A to FIG. 1B). The foot of the patient rests on and is secured at a foot supporting portion 105, which has a plate 104 that can be raised and lowered by electro-mechanical actuators 106 that cause flexion of the foot and enable control of the dorsiflexion angle to a desired setting.

Figure 2:
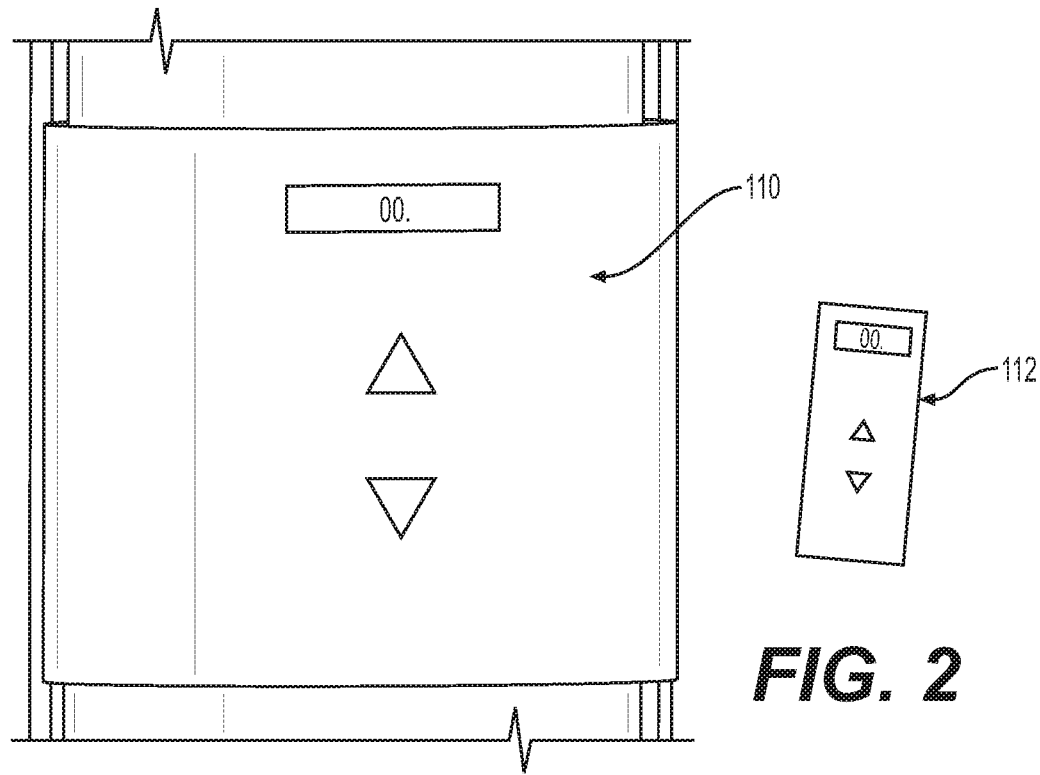
FIG. 2 illustrates details of controls of/for the splint shown in FIGS. 1A-1C.

A control section 110 includes local controls (see up and down arrow buttons, and see also display, shown in further detail in FIG. 2) that allow the patient or clinician to locally and electro-mechanically control the dorsiflexion angle. The control section 110 can be coupled to the actuators 106 to cause the plate 104 to move upwards and downwards for changing flexion. A display readout portion of the control section 110 (showing "00" in the Figures) can be used to display metrics associated with the diagnostics and/or therapeutic settings of the splint, for example to show numerical representations of the tension on the foot (e.g., amount of stretch resistance) and/or a measurement of the dorsiflexion angle.

In the examples provided in the drawings, the actuators 106 are shown as linear actuators, though any electro-mechanical actuator for adjusting the dorsiflexion angle may be used. For example, a rotary motor, such as a stepper motor, may have an off center cam coupled to a drive shaft for raising the plate 104 to a desired dorsiflexion angle. While these examples provide pushing forces to push up on the plate 104 from an underside, other electro-mechanical actuators may supply pulling forces to pull the plate 104 up from a top surface thereof. For example, an electro-mechanical actuator may be configured to shorten or lengthen a strap 221 (shown in FIG. 4) to adjust the dorsiflexion angle as desired. Other examples and variations of the actuators 106 are contemplated by this disclosure to facilitate controlled adjustment of the dorsiflexion angle.

Also shown is a remote control 112, which also includes similar up and down arrows and a display readout portion for the same purposes as those described for control section 110. The remote control 112 may provide a convenient way for a patient or clinician to control function of the splint 100 without having to bend down to the locally-placed control section 110. The remote control 112 can be wired or wirelessly coupled (e.g. via Bluetooth, Wi-Fi, RF, etc.) to the control mechanisms of the splint such as the actuators 106 for controlling flexion. In the embodiment shown in FIGS. 1A-1C, the design of the control section 110 is also shaped such that it can serve as an additional brace or strap for holding the lower leg of the patient in place as desired.

Figure 3:
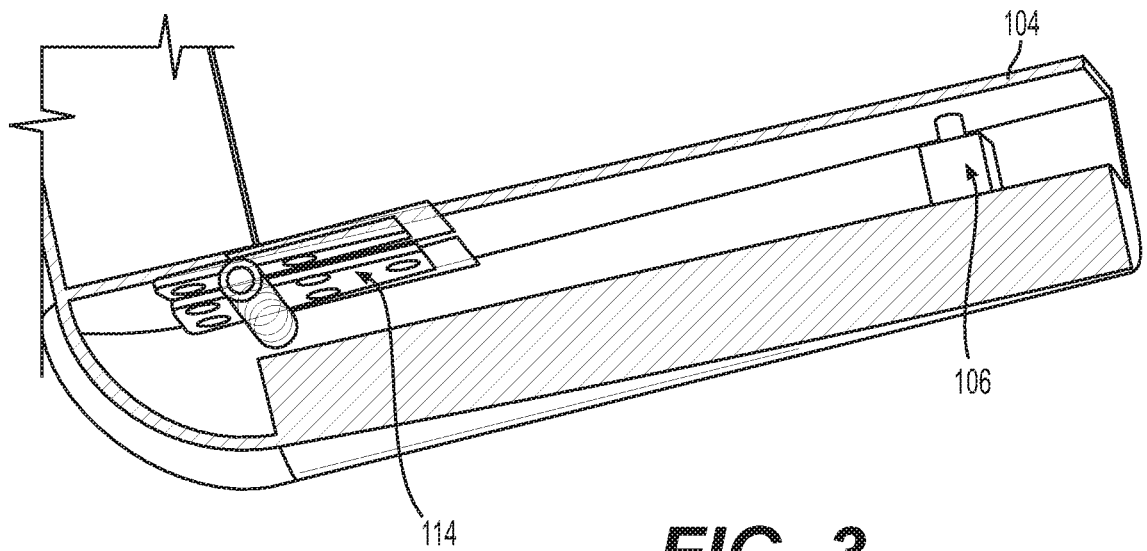
FIG. 3 illustrates a side, cutaway view of a lower portion of the splint shown in FIGS. 1A-1C.

FIG. 3 shows a cutaway view from the side and beneath a portion of the splint 100, and particularly shows the plate 104 and more detail on the actuator 106 that selectively pushes up or moves down to effectuate the setting and/or change in dorsiflexion angle, which is facilitated by the hinges 114 at the opposite end (proximate the location of the heel and ankle of the patient when in use) to enable the end of the plate that is connected to the actuator 106 to move-rotate upwards and downwards. Alternatively or additionally, the angular position can be manually changed for the therapeutic settings without requiring use of the actuator 106 and/or control section 110 or remote control 112. For example, the angle can be changed manually via tightening straps. Alternatively, a lock button can hold the splint in the desired position. In another embodiment, when a motor is present and can be turned manually using a key, the splint can be manually adjusted even with the motor electronics deactivated/off. In the case of a splint without the straps connecting calf to foot pieces (only straps to hold the foot onto the splint), the angle can be moved using a button to activate a motor. In this case, the angle can be varied degree by degree using a button on the brace (a "manual" setting) but a motor is still used to actually change it. An "automatic" setting in this case would be a prescribed angle that is already entered by the physician and the patient presses a button to start movement to the pre-set angle.

Figure 4:
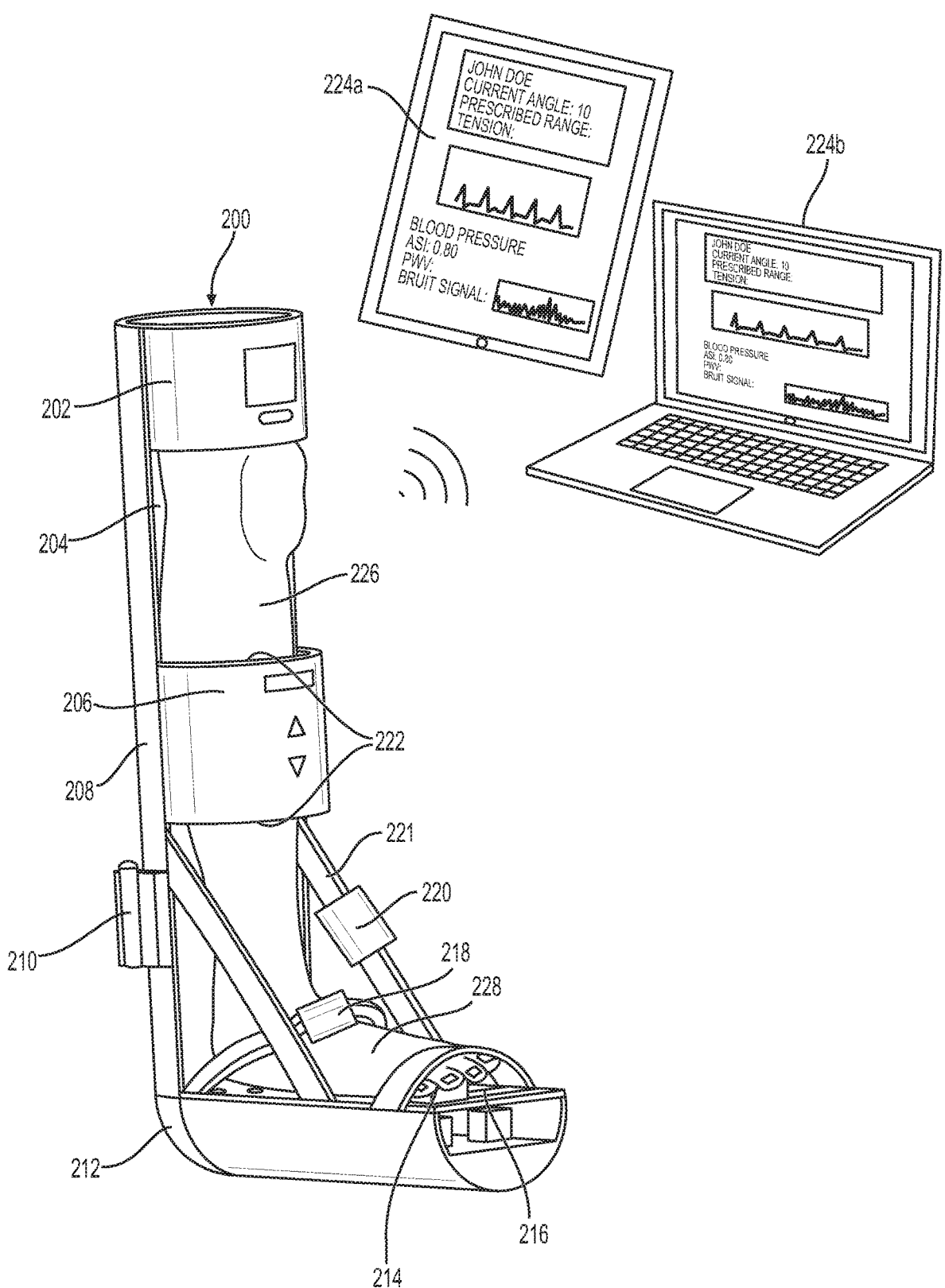
FIG. 4 schematically illustrates a splint according to one embodiment of the present disclosure, with the leg and foot of a patient inserted and secured in the splint.

FIG. 4 schematically shows a splint 200 according to one embodiment of the present disclosure, with the leg 226 and foot 228 of a patient inserted and secured in the splint 200. The splint 200 is shown as part of a system which also includes remote readout/control devices 224a, 224b connected to the splint 200. The splint 200 includes numerous sensing, measurement, and feedback components for performing functions such as monitoring physiological parameters of the patient (e.g., vascular activity-related parameters associated with blood flow, for instance, tension or other force on particular parts of the leg or foot of the patient during use of the splint, etc.) during use of the splint 200 or in a clinical setting, such that a clinician can monitor and change various aspects of the treatment (e.g., dorsiflexion angle) to customize the therapeutic aspects provided by the splint 200 to a particular patient over time for his/her individual needs and progress. The sensing, measurement and/or feedback components (hereinafter also generally referred to as "sensors") may also be used by the patient, in monitoring and controlling their own settings and metrics as they utilize the splint (i.e., in regular use outside of the clinical setting). In some embodiments, machine learning may be utilized for purposes of data fusion and to aid analysis, signal processing, and/or understanding of the physiological parameters or variables utilized in processes described herein.

Among other physiological parameters to be sensed, monitored and/or controlled, the sensors and other functional components of the splint and splint systems described herein can be used with respect to monitoring oxygen saturation via pulse oximetry, pulse, activity in general or specific arteries such as the dorsalis pedis artery or posterior tibial artery, and blood pressure via sphygmomanometry alone in the calf, toe, or as ankle-brachial index (ABI). Also included are one or more of pulse wave velocity (PWV), femoral bruit, skin temperature, and parameters which may be non-invasively measured.

As shown, the splint 200 is connected with devices 224a, 224b, which can be, for example, computing devices such as a tablet computer or smartphone (224a) or a laptop computer (224b) that can be coupled via wired or wireless connections (e.g. via Bluetooth, Wi-Fi, RF, etc.) to the splint 200. The devices 224a, 224b can run executable applications to be utilized for displaying and/or entering data associated with one or more of the measured physiological parameters and one or more of the sensing, measurement and/or feedback components associated with the splint. The devices 224a, 224b may also be used to remotely control the functionality of one or more of these components for affecting the monitoring of various parameters of the patient and/or changing settings of the splint. As shown, and without limitation, the displayed metrics and information on the devices 224a, 224b can include the patient name, dorsiflexion angle ("current angle"), prescribed range (e.g., of angle or tension), blood pressure, ankle-brachial index (ABI), pulse signal and/or rate display, pulse wave velocity (PWV), and bruit signal. Like the embodiment of the splint 100 described above and shown in FIGS. 1-3, as labeled by 212, the splint 200 also has an adjustable dorsiflexion angle, which can be facilitated by the same or similar functional components as those described with respect to the splint 100 (e.g., plate, hinges, actuators, etc. described and shown in FIGS. 1-3).

The splint 200 may be used by clinical personnel in a clinic, such as nurses, physician's assistants, physical therapists, doctors, etc. This Office Splint 200 may record data on a microcontroller or internal memory (e.g., control component 206) which is then wired or wirelessly connected to a computer program or mobile app (e.g., on devices 224a, 224b) in which the clinician can manually input clinical outcome variables such as 6-minute walk test, flow-mediated dilation, and/or ABI which may be manually measured in the clinic as standard of care. This merges manually acquired data with the data obtained by sensors within the Diagnostic Splint 200. Similarly, if the manually acquired data is already entered into an electronic medical record (EMR) or electronic health record (EHR) the data may be merged into the software application with splint recording data automatically via application program interface (API) according to the type of 3rd-party EMR system.

Signal processing algorithms on the devices 224a, 224b process the data received from the Office Splint 200. This allows standardization of datasets for inter-patient and intra-patient analysis. The datasets may be synced by timestamp, standardized in number of datapoints (if applicable), and smoothing and detection algorithms applied to identify trends and features of interest. Calibration algorithms may also be applied to the Office Splint 200 to reset its sensors as necessary. Calibration of received data may also occur to standardize and normalize according to type of data stream.

From time to time calibration with the Office Splint 200 may be necessary. In this process, the unworn splint undergoes a known pattern, such as dynamic flexion of the unworn splint at a set rate and angle or a static test without movement. The app facilitates a clinician or technician to interface with the splint 200 during these processes, which is also sometimes necessary for Home Splints which are outfitted with monitoring sensing systems, described in more detail below.

The splint 200 includes: a blood pressure cuff 202; embedded sensors for bruit 204; angle display and control components (204) (see discussion above of similar components 110 shown in FIGS. 1-2); near infrared spectroscopy (NIRS) sensor 208 embedded in the splint (or adhered to the skin on the calf or another area of interest); and a Doppler ultrasound device or tonometer 210. In some implementations, one or more of the components of the splint 200 may optionally not be included. For example, in some implementations one or more of the blood pressure cuff 202, sensors for bruit 204, or tonometer 210 may optionally not be included on the splint 200.

By "bruit" is meant the sound made by blood passing through major arteries. Various pathologies of the vasculature can change these sounds and thus indicate abnormalities of the artery. Disclosed herein is a quantitative measurement of the vibration/acoustic and records and feeds into a machine learning algorithm. After sufficient training data is gathered, differences in the sound/vibration patterns and can be associated with clinical vascular changes to aid in overall diagnosis. This type of machine learning approach can apply to any single measurement or combination of measurements that best help inform the diagnostic recommendation. Algorithms that may apply include regression statistics, Bayesian statistics, neural networks (supervised or unsupervised), and support vector machines. NIRS is a non-invasive measurement of muscle oxygenation. This helps identify oxygenation before, during, and after different levels of dorsiflexion applied by the splint to aid in diagnostics.

Infrared wavelengths of light are passed into the tissue and absorbance coefficients are calculated based on attenuation of the light within the tissue. Wavelength and source/detector design determine depth of measurement. The tissue saturation index can also be calculated as a ratio of oxygenated hemoglobin and myoglobin to total hemoglobin/myoglobin.

In some implementations, the NIRS sensor 208 is used to measure one or more of tissue oxygenation (oxyhemoglobin (O2Hb) and deoxyhemoglobin (HHb), and total tissue hemo (+myo)globin (tHb). The NIRS sensor 208 may be positioned to measure a decrease in blood flow to acutely stretched plantar flexor muscles, such as the soleus and/or gastrocnemius muscles. In an implementation, the NIRS sensor 208 or an additional NIRS sensor (not shown) may be positioned on a toe positioned within the splint 200.

In one example, the NIRS sensor may be a MOXY MONITOR produced by Fortiori Design LLC, Hutchinson, Minn., which utilizes 4 wavelengths of light, at 680, 720, 760, and 800 nm. The NIRS sensor 208 contains a single LED and two detectors placed 12.5 and 25.0 mm from the LED source. The NIRS sensor 208 provides the oxygenation measurements (e.g., O2Hb, HHb, and/or tHb) using a spatial resolution approach. Thus the NIRS sensor 208 is especially useful to examine microcirculation (capillaries, arterioles, and venules) as it is completely absorbed in vessels larger than 1 mm due to the high concentration of hemoglobin.

The NIRS sensor 208 reliably assesses the degree of stretch (e.g., dorsiflexion angle) that maximizes the decrease in intramuscular blood flow without causing intolerable discomfort to a patient. Specifically, the NIRS sensor 208 assesses a degree of acute ankle dorsiflexion that leads to a maximal decrease in muscle oxygenation in each patient before beginning a prescribed stretching program. In some implementations, the muscle oxygenation measurements from the NIRS sensor 208 are displayed on one or more of the remote readout/control devices 224a, 224b connected to the splint 200. Accordingly, a clinician is facilitated to review the muscle oxygenation measurements from the NIRS sensor 208 and adjust the dorsiflexion angle through the actuator 106, control section 110, and/or remote control 112 to achieve a maximal decrease in muscle oxygenation. In an implementation, the control section 106 or an application on the remote readout/control devices 224a, 224b is configured to receive measurements from the NIRS sensor 208 and automatically adjust the dorsiflexion angle to achieve a maximal decrease in muscle oxygenation, such as through a proportional-integral-derivative (PID) control algorithm, P, PI, bang-bang, or other such system control algorithm known to those of ordinary skill in the art.

The Doppler ultrasound device 210 can be configured for imaging, to measure flow velocity, for ABI calculation, and/or waveform evaluation, among other aspects. It should be noted that for the sensors described herein in accordance with this embodiment, not all of the sensors are required to be active at all times; many of the sensors can be used individually or in combination, and some purposes may overlap; for example, the photoplethysmogram 214 on the toe can be used for measuring pulse oximetry, blood pressure, and/or pulse wave velocity.

The splint 200 also includes a tensiometer 220 on a strap 221, shown on one side of the splint 200 from the leg supporting portion to the foot supporting portion of the splint. It can be critical in the treatment of PAD to ensure that the tension applied to the leg (calf muscles in particular, and related physiology) by the flexion imposed by the splint does not exceed a clinically-desired level or a level which causes damage or unnecessary amounts of pain to the patient. The optional strap 221 with the tensiometer (and/or other components of the splint 200 which affect and control the tension applied for treatment) can also be configured to enable a change in the dorsiflexion angle to stop (for example for any automated adjustment of the angle to cease) if the tension as measured by the tensiometer 200 exceeds a detrimental amount or level or otherwise exceed a threshold tension. As shown, the splint also includes plantar pressure measurement sensors 216, dorsalis pedis sensors 218, and skin temperature sensors 222.

The plantar pressure measurement sensor 216 may be resistive, capacitive, piezoelectric, etc. The purpose is to measure how much the limb is stretched by measuring the amount it pushes onto the splint as the dorsiflexion angle is increased (particularly the distal end). It is an analogous way to measure tension in the flexed limb by measuring push of the foot along the bed of the splint rather than tension of a strap. In this case, the splint may not have straps connecting the calf portion to the foot portion as means of adjusting and/or measuring tension. In one embodiment, the splint can have straps to comfortably hold the patient's foot onto it. This allows for the patient's amount of stretch to be measured during diagnosis or therapy.

Skin temperature can be a useful variable to link to overall vascular function of the limb, especially when combined with other variables in diagnostic algorithms. Skin temperature may be taken as an absolute or relative measure. It has been referenced as a qualitative measure to help determine PAD by placing a hand on each leg to qualitatively determine if a difference is felt. Disclosed herein is a device for quantitatively measuring temperature, and this information can be combined with other variables.

Figure 5:
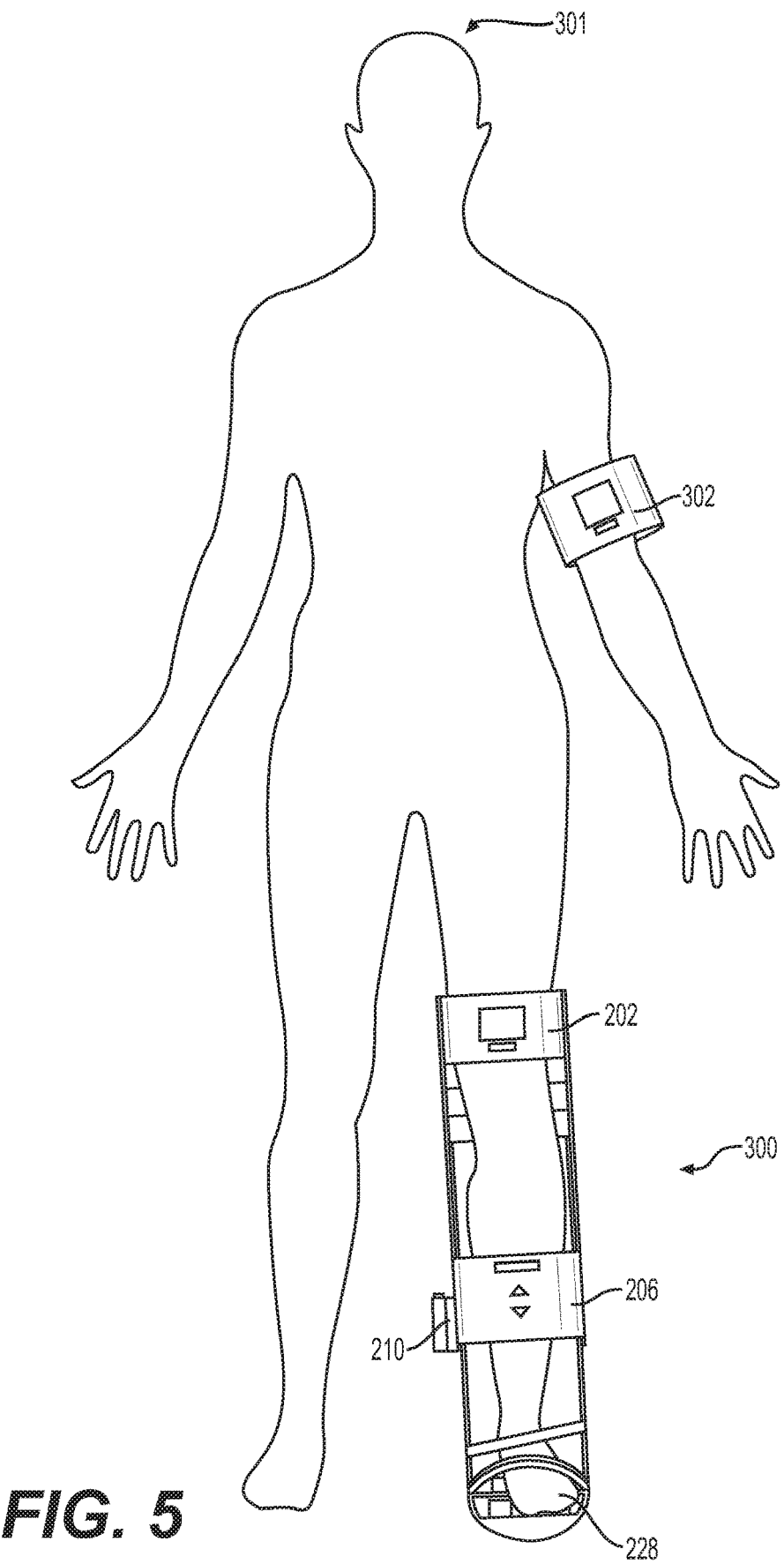
FIG. 5 schematically illustrates a splint system according to one embodiment of the present disclosure, with a patient wearing a leg splint and a separate brachial cuff.

FIG. 5 schematically illustrates a splint system according to one embodiment of the present disclosure, with a patient 301 wearing a leg splint 300 with a segmental cuff 202 and a separate brachial reference cuff 302 worn on the arm of the patient 301. The splint 300 shown in FIG. 5 includes some or all of the components included in the splint 200 shown in FIG. 4. For reference, the blood pressure cuff 202, angle display and control component 206, and doppler ultrasound or tonometer 210 are labeled. In some implementations, one or more of the blood pressure cuff 202 or tonometer 210 may be separately provided from the splint 200 or not used. The brachial cuff 302 can be used as a reference for comparison to blood pressure measurements made at the cuff 202. ABI is a standard clinical measure that uses a ratio between the brachial pressure and the ankle pressure as a measure of disease severity. It is the most common clinical variable currently used to diagnose PAD. The device disclosed herein can include this capability or it can be used simultaneously with already-existing ABI systems that automatically take ABI measurements.

Figures 6A, 6B:
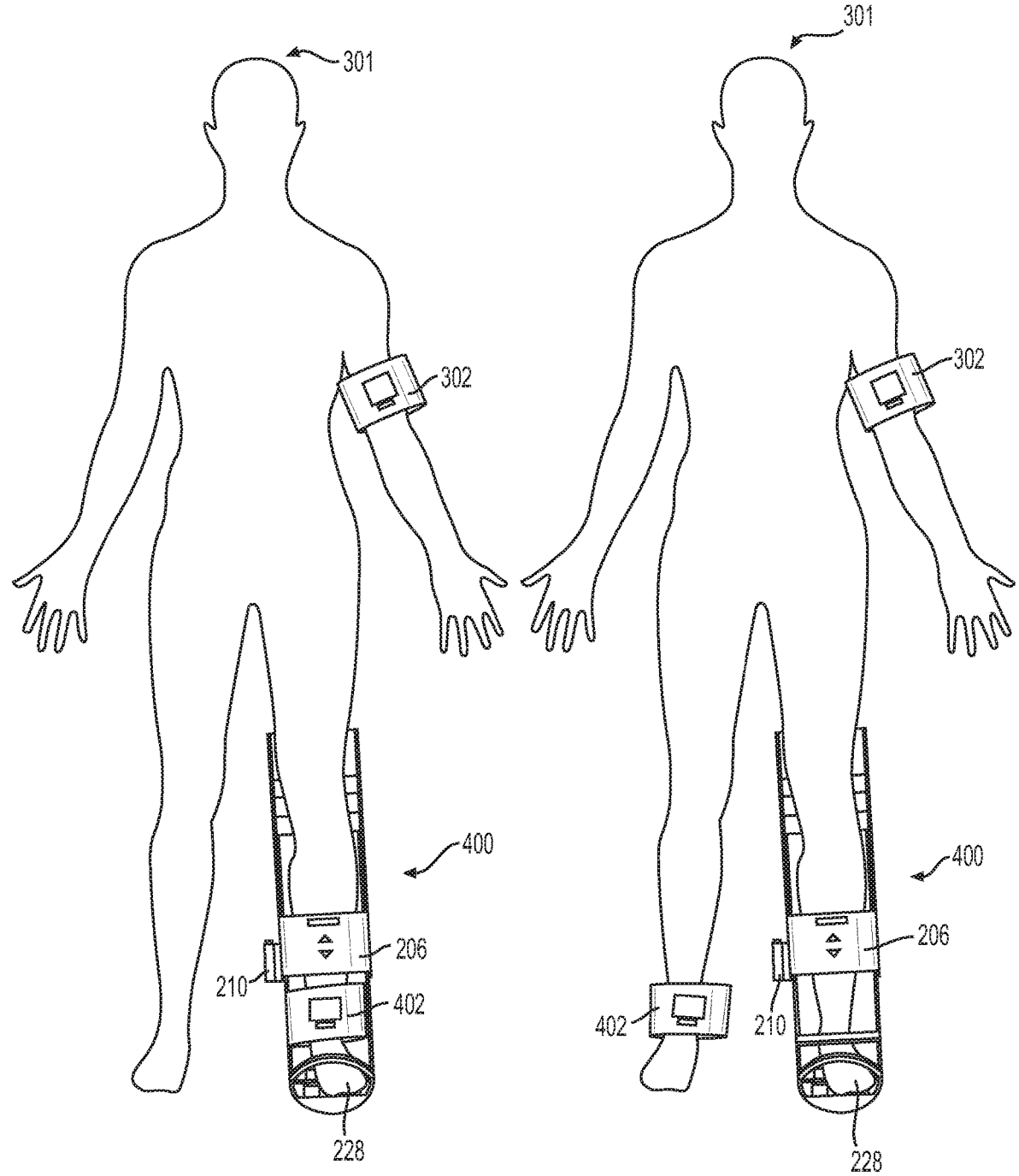
FIGS. 6A and 6B schematically illustrate a splint system according to one embodiment of the present disclosure, with a patient wearing a leg splint and brachial cuff, and also including an ankle cuff.

FIGS. 6A and 6B schematically illustrates a splint system according to one embodiment of the present disclosure, with a patient wearing a leg splint 400 along with an ankle cuff 402 and brachial cuff 302. The splint 400 shown in FIGS. 6A and 6B includes some or all of the components included in the splint 200 shown in FIG. 4 and FIG. 5. For reference, the angle display and control component 206, doppler ultrasound or tonometer 210, and brachial cuff are labeled. In FIG. 6A, the patient 301 is wearing the ankle cuff 402 on the splinted leg, whereas in FIG. 6B, the ankle cuff 402 is worn on the other leg.

The ankle cuff 402, brachial cuff 302, and/or a standard cuff as part of the brace (see, e.g., 202 of FIG. 5) can be utilized for clinical ABI and/or pulse wave velocity measurement while wearing the brace. The ankle cuff can be used to determine blood pressure at the ankle which can also be described as a segmental pressure. The brachial cuff is closer to the heart and measures brachial pressure. Together the ankle and brachial serve as a comparative measure of vascular function at different distances from the heart through the Ankle-Brachial Index (ABI), the most accepted clinical diagnostic measure of PAD. In some implementations, one or more of the cuffs may be separately provided from the splint 200, 300, 400 or not used in conjunction with the splint 200, 300, 400.

Figure 7:
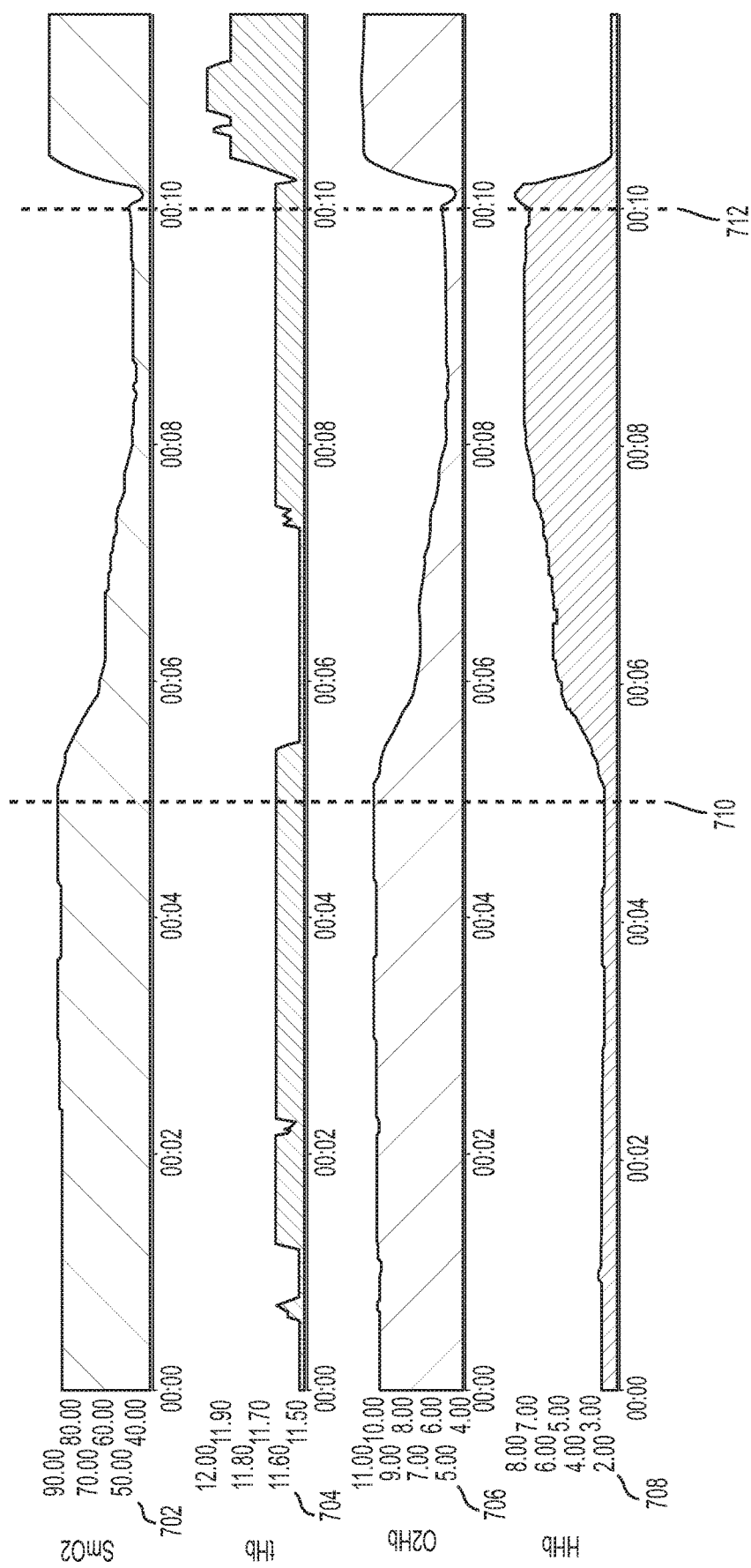
FIG. 7 illustrates timing diagrams of measurements from a near-infrared spectroscopy sensor (NIRS) sensor.

FIG. 7 illustrates timing diagrams of measurements from a near-infrared spectroscopy sensor (NIRS) sensor upon application of a splint, such as any of splints 100, 200, 300, or 400 described above, to induce dorsiflexion stretching. The NIRS sensor readings are measurements of physiological parameters of one or more plantar flexor muscles, such as the soleus and/or gastrocnemius muscles. A tissue oxygenation curve 702 shows a percentage of measured tissue oxygenation (SmO2) over time. A total hemoglobin curve 704 shows a total amount of hemoglobin (tHb) in the measured muscle expressed in grams per deciliter (g/dl) over time. An oxygenated hemoglobin curve 706 shows an amount of oxygenated hemoglobin (O2Hb) in the measured muscle expressed in g/dl over time. A deoxygenated hemoglobin curve 708 shows an amount of deoxygenated hemoglobin (HHb) in the measured muscle expressed in g/dl over time.

As shown in FIG. 7, times occurring before a first time 710 designate measurements of a leg at rest in neutral position where no stretching is applied. At the first time 710, application of dorsiflexion via splinting is applied. In the example shown in FIG. 7, dorsiflexion is applied at a 15° angle. After the first time 710, the oxygenated hemoglobin curve 706 shows a decrease in O2Hb while the deoxygenated hemoglobin curve 708 shows an increase in HHb. For example, the O2Hb falls from a baseline level of about 10 g/dl Hb to a reduced level of about 5 g/dl Hb. Likewise, the HHb increases from a baseline level of about 2 g/dl Hb to an increase level of about 7 g/dl Hb. At the same time, the total hemoglobin curve 704 experiences a dip in tHb after dorsiflexion is applied before normalizing back to a baseline level, indicating a level of ischemia present in muscle tissue. For example, the tHb dips from a baseline level of about 11.6 g/dl Hb to a reduced level of about 11.5 g/dl Hb. The tissue oxygenation curve 702 shows a decrease in SmO2 from a baseline level of about 85% to a reduced level between 40-50%.

At a second time 712, dorsiflexion is released where each of SmO2, O2Hb, and HHb show recovery of tissue oxygenation and return to baseline levels while tHb experiences an increase over baseline levels, which indicates the acute reactive hyperemic effect. For example, the tHb increases from the baseline level of 11.6 g/dl Hb to between 11.8-12 g/dl Hb. In the example shown, a difference between the second time 712 and the first time 710 is 5 minutes. Other amounts of times may be used for applying dorsiflexion, such as 1, 2, 3, 4, 6, 7, 8, 9, 10 or more minutes. In the example shown in FIG. 7, baseline systemic pulse oximetry was also recorded during splinting via finger pulse oximeter, which indicated no change in baseline arterial oxygenation.

As described above, the NIRS sensor measurements can be wired or wirelessly reported wirelessly in real time to the control section 106 or an application on the remote readout/control devices 224a, 224b for logging or real-time display. Using the NIRS sensor measurements, such as those shown in FIG. 7, a clinician may adjust the dorsiflexion angle to identify a degree of acute ankle dorsiflexion that leads to a maximal decrease in muscle oxygenation in each patient before beginning a prescribed stretching program. For example, dorsiflexion may be initially applied at a 5° dorsiflexion angle and NIRS sensor measurements monitored for a period of time (e.g., 1-5 minutes) to determine an amount of decrease in muscle oxygenation. The clinician increases the dorsiflexion angle, such as in 1-5° degree increments, and likewise monitors an amount of decrease in muscle oxygenation following each dorsiflexion angle increment. The clinician may continue increasing the dorsiflexion angle up to a maximum dorsiflexion angle, such as between 20-30°. The clinician may then prescribe a dorsiflexion angle to a patient to be the smallest dorsiflexion angle at which a maximal decrease in muscle oxygenation. Alternatively, the clinician may continue increasing the dorsiflexion angle until either further decreases in muscle oxygenation are not seen in the measurement or the patient experiences intolerable discomfort. In a further alternative, the clinician may continue increasing the dorsiflexion angle until a threshold decrease in muscle oxygenation is measured (e.g., until muscle oxygenation is less than 50% or until at least a 30-40% decrease in baseline oxygenation levels are measured).

While the example of FIG. 7 relies on a NIRS sensor to monitor muscle oxygenation, blood flow may also be monitored via perfusion magnetic resonance imaging (MRI), such as pseudo-continuous arterial spin labeling (p-CASL), continuous arterial spin labeling (CASL) where tagged blood is imaged as it moves through the imaging region, in this case the musculature of the calf. This allows examination of large arteries as well as changes in microcirculatory regions within skeletal muscle itself. Blood Oxygen Level Dependent (BOLD) MRI is dependent on changes in oxygenated and deoxygenated hemoglobin and relies on the paramagnetic properties of deoxygenated hemoglobin. This type of imaging introduces a delay in imaging of a few seconds.

Figure 8:
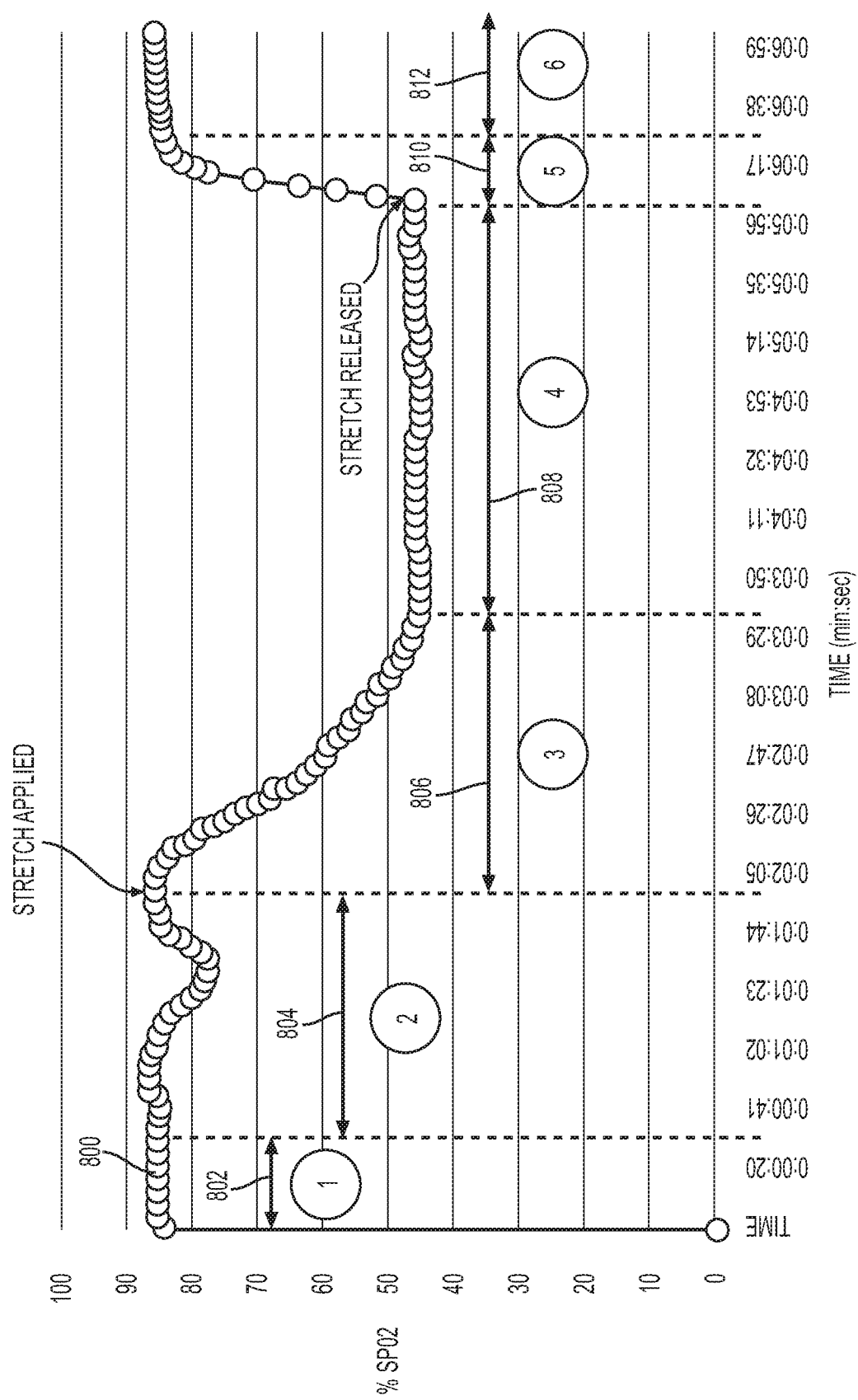
FIG. 8 illustrates a timing diagram of muscle oxygenation during dorsiflexion splinting measured by a NIRS sensor measurement of the gastrocnemius.

FIG. 8 illustrates a timing diagram 800 of muscle oxygenation during dorsiflexion splinting measured by a NIRS sensor measurement of the gastrocnemius. During a first time period 802 (1) a baseline muscle oxygenation measurement is established with a patient's leg at rest. During a second time period 804 (2) adjustment of the splint is made. During a third time period 806 (3) a maximum dorsiflexion is applied via the splint. During a fourth time period 808 (4) a maximum percentage of muscle oxygenation drop is achieved, evidenced by the plateau. In the example shown in FIG. 8, the maximal percentage of muscle oxygenation drop is achieved at a level between 40-50% muscle oxygenation (e.g., less than 50% muscle oxygenation). During a fifth time period 810 (5) the splint is released. During the sixth time period 812 (6) full recovery of muscle oxygenation back to resting baseline is measured.

Using a determined dorsiflexion angle based on the measurements shown in FIGS. 7 and/or 8, a clinician prescribes a stretching program that should be applied by a patient. The stretching program prescribes intensity (e.g., angle of dorsiflexion stretching), frequency (e.g., daily, twice daily, every other day, at least 5 days per week, etc.), and duration of muscle stretching intervention (e.g., 1-30 minutes). Periodically, such as after 1-4 weeks, the patient may be re-evaluated by the clinician and the stretching program may be adjusted to ensure the stretching program maintains a degree of acute ankle dorsiflexion that leads to a maximal decrease in muscle oxygenation.

Other clinical tests and measurements may be taken as part of prescribing and evaluating the stretching program. Measurements of clinical outcomes before, during, and/or after treatment may be collected. These measurements may be assessed separately within the clinic in addition to measurements taken with the diagnostic splint and used to assess patients for appropriate level of stretching intervention. The clinical outcomes measurements may include one or more of ABI, both resting and post-exercise; a 6-minute walk test; patient characteristics determined during standard care or by questionnaire/survey; a level of frailty assessment; physical function tests, such as activities of daily living; comorbid diagnoses, e.g. diabetes mellitus, foot ulcers, chronic obstructive pulmonary disease, or cardiovascular disease; a lifestyle assessment; and other intervention assessment, e.g. pharmaceutical treatments, exercise programs, or physical therapy.

To aid in these clinical measurements, various measurement techniques and technologies may be used. The following techniques are based on optical interaction with tissue and are often differentiated by the wavelengths used, the methods of calculation, and consequently can be tailored for general vs. local measurement, precision, and tissue depth.

Photoplethysmography (PPG) is an optical technique used to sense changes in blood volume in microcirculation of tissue, especially close to the sensor interface based on use of wavelengths in the red or near infrared spectrum. When wavelengths such as 800 nm are used, PPG is largely unaffected by blood oxygenation levels. An emitter and a detector are used to produce a PPG waveform. The design may be trans-illumination with the body part between the emitter and detector, or may be configured in a reflective setup where emitter and detector are located side by side. The PPG waveform is affected by cardiovascular pulsation, often called the "AC component" which changes as the distance from the heart increases or as affected by a disease state. The PPG baseline or "DC component" is influenced by many complex factors such as thermoregulation, respiratory state, humoral effects, and sympathetic nerve activity. PPG can be used to approximate blood pressure, and therefore may be used in combination with a brachial PPG for estimation of ABI. PPG waveforms are also useful for extraction of features indicative of level of disease progression in PAD patients. Furthermore, PPG may be used for estimation of arterial stiffness by comparing upstream and downstream waveforms and calculating pulse wave velocity or pulse transit time. The level of arterial stiffness may indicate level of disease as it is related to level of occlusion, plaques, and endothelial function.

With near-infrared spectroscopy two or more wavelengths of light are used to assess oxygenation within deeper tissue. Typically, measurement depth is 1-3 cm. A modified Beer-Lambert law is used to calculate the oxygenated and deoxygenated hemoglobin present within the measurement area based on the intensity of the optical signals. The emitter LED and the photodetector are placed side by side a set distance apart, which is also dependent on the wavelengths used due to tissue scattering. In an implementation, a NIRS system with 4 wavelengths of light measures oxygenated vs. deoxygenated hemoglobin based on modeling the light interaction with tissue. The total hemoglobin can also be calculated using NIRS methods.

With pulse oximetry two wavelengths of light are emitted and measured as they interact with tissue to yield a measure of oxygenation. Like PPG, pulse oximetry (PO) may be trans-illumination (emitter-toe-detector setup) or may use reflectance in a side by side configuration. PO yields blood oxygenation values in relative terms, and therefore total hemoglobin is not measured as it is with NIRS.

Blood pressure, particularly segmental pressures compared to brachial pressure, are the most accepted method for diagnosis of peripheral arterial disease. Blood pressure as measured at the ankle is most clinically accepted, where a cuff is applied at the base of the leg.

The dorsalis pedis or posterior tibial artery are monitored via doppler ultrasound or tonometer to indicate the maximum pressure present in the monitored artery as pressure is released from the cuff after full arterial occlusion.

To determine a patient's Ankle-Brachial Index (ABI), the maximum pressure recorded in the leg of interest is compared to the maximum blood pressure as measured in both arms via the brachial artery. The ABI is determined as a ratio between the ankle pressure to brachial pressure. ABI is the usual standard for diagnosis of peripheral arterial disease and classification of severity. Ankle-brachial index generally decreases with disease severity. Both the Rutherford and Fontaine scales are commonly-referenced scales to relating symptoms to disease progression.

Pulse Volume Recording (PVR) and/or segmental pressures, such as calf blood pressure and plethysmography as measured with a cuff placed below the knee, or toe blood pressure as a final distal measure of blood pressure changes in the limb may also be clinically useful. When recorded as pressure waveforms, changes in features such as presence/loss of dichrotic notch, loss of amplitude, and general flattening of the waveform or an absence of the waveform in cases of incompressibility due to severe calcification. Segmental pressures may be measured at various locations such as high thigh, low thigh, calf, ankle, and foot.

Pulse Wave Velocity (PWV) or Pulse Transit Time (PTT) may be non-invasively recorded from doppler, tonometer, or photoplethysmography-based measurements as features on an upstream pulse are assessed relative to a peripheral pulse, particularly in vessels of the extremity, e.g. brachial artery and dorsalis pedis. The distance of between the measurement points is known and is used to calculate the pulse wave velocity. PWV is a measure of arterial stiffness and has been shown to be correlated with vascular damage and atherosclerosis. PAD is a disease involving atherosclerosis in the extremities.

Tissue oxygenation of local muscle area, which is affected by the vascular delivery via resistance vasculature, as well as the metabolic demand and use of aerobic metabolic pathways, which are changed in peripheral arterial disease compared to healthy muscle.

Other clinical assessments or measurement techniques may be used.

Based on the prescribed stretching program determined using a clinical splint, such as any of splints 100, 200, 300, or 400 described above, a therapeutic splint may be provided to the patient. The therapeutic splint comprises a mechanical stop adapted to prevent the dorsiflexion angle provided by the splint to be greater than the prescribed dorsiflexion angle in the stretching program. In other words, the mechanical stop is adapted to prevent the angle between a foot support surface and a leg support surface on the therapeutic splint from decreasing beyond a prescribed dorsiflexion angle. For example, the clinician may configure the therapeutic splint to set the mechanical stop to be at an angle equal to the prescribed dorsiflexion angle in the stretching program. FIGS. 9-16 provide various exemplary implementations of therapeutic splints in accordance with the teachings of this disclosure. While particular examples are provided herein, this disclosure is not limited to the examples provided herein.

Figure 9:
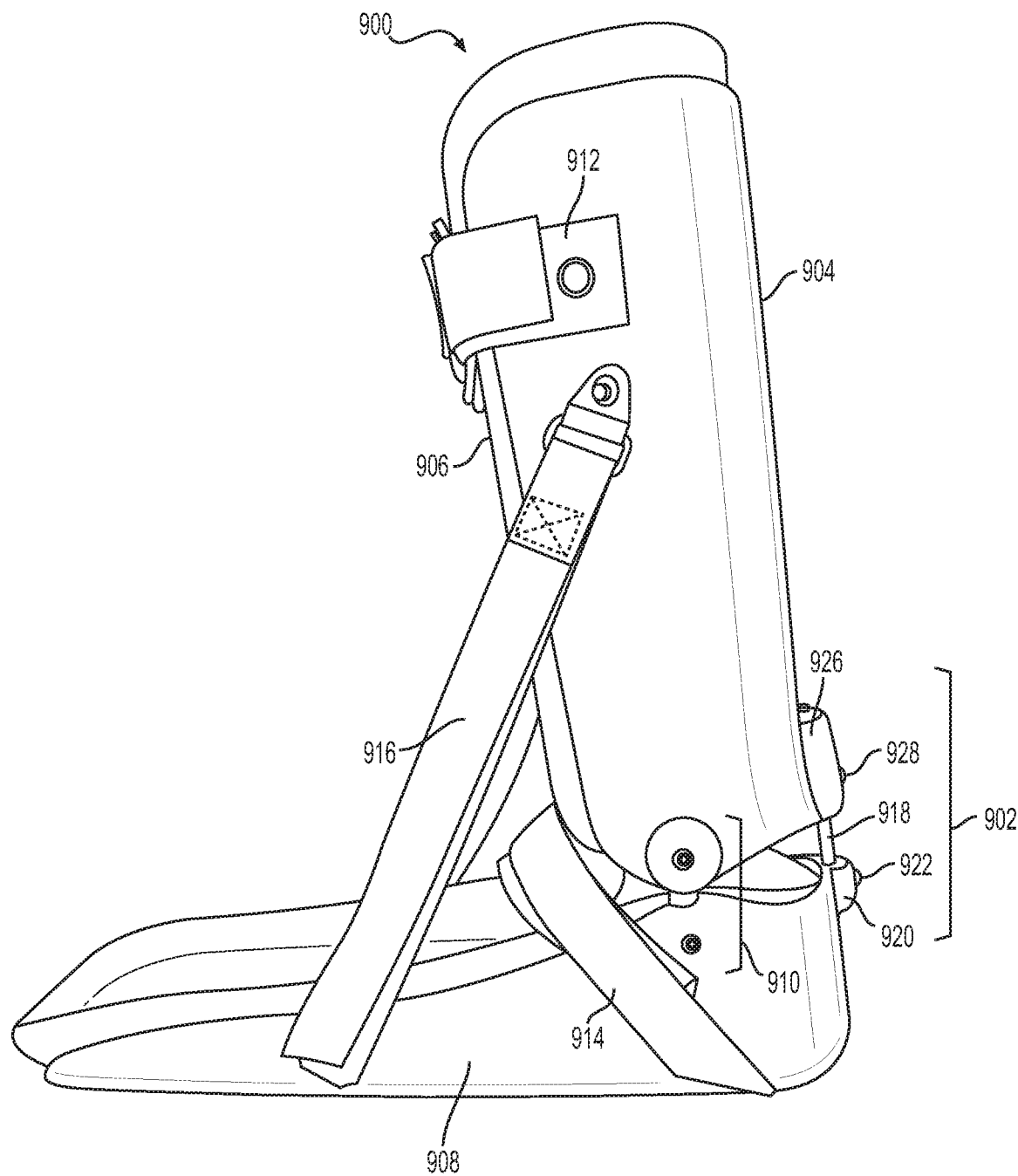
FIG. 9 illustrates a therapeutic splint with a posterior dorsiflexion limiter.

FIG. 9 illustrates a therapeutic splint 900 with a dorsiflexion limiter 902. The splint 900 comprises a leg support surface 904 that defines a cavity 906 for receiving a lower leg of a patient. In the example shown in FIG. 9, the leg support surface 904 comprises a u-shaped cross section, though other cross-sectional shapes may be used such as a v-shaped or square-shaped cross section.

The splint 900 also comprises a foot support surface 908 adapted to receive a plantar portion of a foot of the patient. In the example show in FIG. 9, the foot support surface 908 comprises a heel cup and raised sides for securely maintaining the foot of the patient therein, though in some implementations, the foot support surface 908 may be substantially flat. A hinge 910 couples the foot support surface 908 at the heel cup to a side surface (e.g., a side of the u-shaped surface spaced apart from a longitudinal inflection along the length of the leg support surface 904) on the bottom of the leg support surface 904. In the example shown in FIG. 9, the hinge 910 comprises a pivot point on each of the foot support surface 908 and the leg support surface 904. In some implementations, the hinge 910 may be fixedly coupled to in integrated on one of the foot support surface 908 or the leg support surface 904 and rotationally coupled via a pivot to the other of the foot support surface 908 or the leg support surface 904. A second hinge (not shown) couples the foot support surface 908 on the other side of the heel cup opposite from the hinge 910 to a side surface opposite the cavity 906 on the bottom of the leg support surface 904.

The hinge 910 and the second hinge rotationally couple the foot support surface 908 to the leg support surface 904 to facilitate dorsiflexion and plantar flexion (e.g., release of dorsiflexion) while minimizing motion in other planes. In other words, the hinge 910 and the second hinge facilitate rotation of the foot support surface 908 relative to the leg support surface 904 between a first configuration and a second configuration. In the first configuration, the foot support surface 908 is at a first angle to the leg support surface 904. For example, the first angle may be between 80-100°, typically at approximately 90°. In the second configuration, the foot support surface 908 is at a second angle to the leg support surface 904, where the second angle is less than the first angle.

The leg support surface 904 and the foot support surface 908 are constructed of rigid materials, such as a rigid plastic, wood, metal, ceramic or other such rigid materials to maintain proper placement and alignment of a patient's leg and foot within the splint 900. In the example shown in FIG. 9, the leg support surface 904 and the foot support surface 908 are line with a foam liner. Other liner materials may be used, such as a gel or fabric liner. In some implementations, one or both of the leg support surface 904 and the foot support surface 908 may not have a liner material.

Straps provide a low cost and effective mechanism for maintaining the leg position in the splint 900, that is heel placed in the back of the heel cup on the foot support surface 908 and the leg support surface 904 maintains contact with the lower leg for alignment therebetween. In the example shown in FIG. 9, the splint 900 includes a leg strap 912 and an ankle strap 914. The leg strap 912 extends from a first side to a second side of the leg support surface 904 across the cavity 906. The ankle strap 914 extends from a first side to a second side of the foot support surface 908, across the heel cup in the example shown in FIG. 9. In some implementations, additional straps may be included. For example, a foot strap across an end of the foot support surface 908 opposite from the heel cup to maintain positive contact between a patient's foot and the foot support surface 908. In another example, one or more straps may extend around a patient's leg above their knee to maintain the patient's leg in an extended position.

A dorsiflexion strap 916 is coupled between the leg support surface 904 and the foot support surface 908 to maintain dorsiflexion when tightened and release dorsiflexion when loosened. As the dorsiflexion strap 916 is tightened, the dorsiflexion angle increases. While the dorsiflexion angle increases, an angle between the foot support surface 908 and the leg support surface 904 decreases. The dorsiflexion strap 916 is coupled to a first side of the leg support surface 904 at a location spaced apart from the hinge 910 more than half the length of the leg support surface 904. Likewise, the dorsiflexion strap 916 is coupled to a first side of the food support surface 908 at a location spaced apart from the hinge 910 more than half the length of the foot support surface 908. A second dorsiflexion strap (not shown) is coupled between the leg support surface 904 and the foot support surface 908 on a side opposite from the dorsiflexion strap 916.

The leg strap 912, the ankle strap 914, and the dorsiflexion strap 916 are adjustable length straps shown in the example of FIG. 9 as a cinch strap with a hook and pile cloth anchor for maintaining a desired length, though other types of straps may be used. Other anchor mechanisms may be used, such as buttons, buckles or the like for maintaining a strap at a desired length. The straps may alternatively or additionally be a side release buckle strap, a cam buckle strap, a lashing strap, a ratchet strap, or other such adjustable length strap or buckle. In the example shown in FIG. 9, each of the leg strap 912 and the ankle strap 914 comprise padding adapted to maintain contact between the strap and a patient's leg or ankle. Any additional straps that make contact with a patient's leg or foot may additionally include padding at the patient contact locations.

In the example shown in FIG. 9, the splint 900 is an anterior entry splint where the cavity 906 of the leg support surface faces towards an extended end of the foot support surface 908. Accordingly, an anterior side of the splint 900 is a side of the splint 900 towards which the cavity 906 faces (e.g., the "left" side of FIG. 9 as shown). Likewise, a posterior side of the splint 900 is a side of the splint 900 opposite from which the cavity 906 faces (e.g., the "right" side of FIG. 9 as shown).

As shown in FIG. 9, the dorsiflexion limiter 902 is mounted at the posterior side of the foot support surface 908, such as on a back surface of the heel cup. The dorsiflexion limiter 902 prevents the dorsiflexion angle from exceeding a maximum dorsiflexion angle such that the splint 900 achieves a prescribed dorsiflexion of the foot. In other words, the dorsiflexion limiter 902 prevents the angle between the foot support surface 908 and the leg support surface 904 from being reduced beyond a minimum angle.

In the example of FIG. 9 (and FIGS. 10A and 10B), the dorsiflexion limiter 902 includes a bar 918 with an enclosed slot 924 therethrough. The bar 918 has a fixed end and a sliding end. The fixed end of the bar 918 is positioned within a housing 920 and fixedly located therein via a locking pin 922. The locking pin 922 may be a screw, rivet, bolt, or other such pin for affixing the fixed end of the bar 918 to the housing 920. Other means of affixing the bar 918 to the housing 920 may be used, such as gluing or welding.

A sliding end of the bar 918 is positioned within a housing 926 in a sliding relationship. For example, the housing 926 comprises a groove (not shown) within which the bar 918 is received and slides along. A dorsiflexion stop 928 is positioned through the slot 924 along a length of the housing 926 for limiting an extent that the housing 920 and the housing 926 may be separated. The dorsiflexion stop 928 may be a screw, rivet, bolt, or other such pin for affixing to the housing 926 through the slot 924. In some implementations, the housing 926 comprises a plurality of pre-established locations (e.g., pre-drilled holes) for insertion of the dorsiflexion stop 928 at regular dorsiflexion angle increments (e.g., every 5° of dorsiflexion). Working in conjunction with the hinge 910, the dorsiflexion stop 928 establishes a limit for the maximum dorsiflexion angle. In other words, the dorsiflexion stop 928 limits how much less the angle between the foot support surface 908 and the leg support surface 904 may decrease.

Figure 10A:
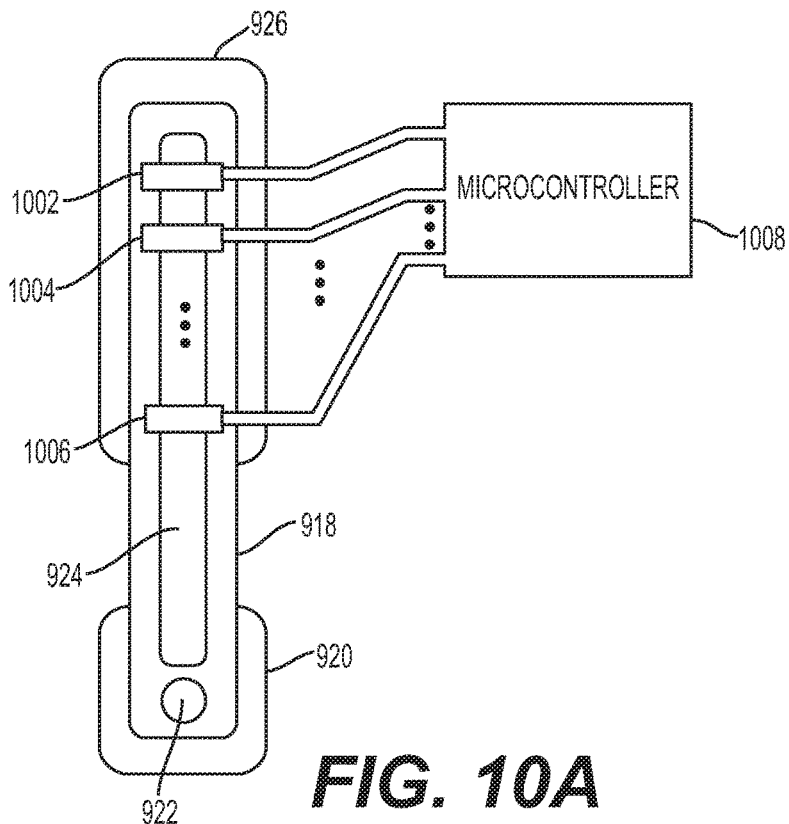
FIGS. 10A and 10B illustrate the posterior dorsiflexion limiter at a rest position and a stretched position with patient compliance sensors.
Figure 10B:
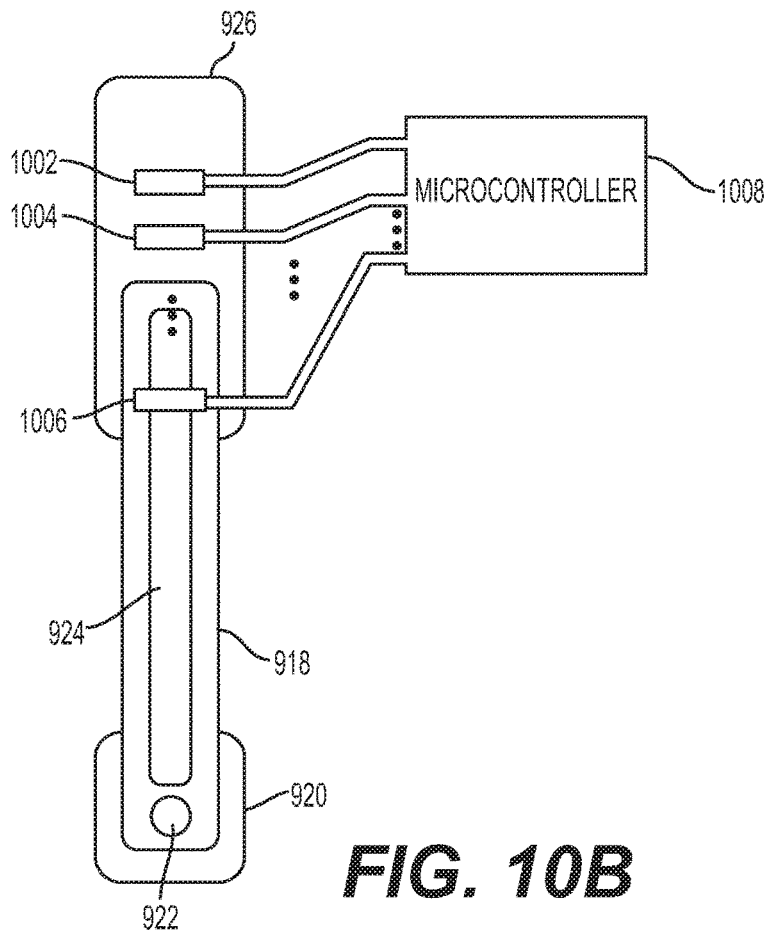

In the example shown in FIGS. 9, 10A, and 10B, the housing 920 is located on the foot support surface 908, such as at the ankle cup and the housing 926 is located on the leg support surface 904. In some implementations, the location of the housing 920 and housing 926 may be reversed.

As shown in FIGS. 10A and 10B, one or more patient compliance sensors may be integrated into the splint 900. For example, within the housing 926 of the dorsiflexion limiter 902, one or more sensors may be placed at regular intervals along a path of the bar 918. Each sensor may span across a width of the slot 924 in the bar 918 and sense whether the bar 918 is present at a respective sensor location. For example, a first sensor 1002 is positioned at a first location in the housing 926 for sensing when the bar 918 is fully inserted into the housing 926 (e.g., the foot support surface 908 is at approximately a 90° angle to the leg support surface 904). A second sensor 1004 is positioned at a second location in the housing 926 at an intermediate location along a path of the bar 918. A third sensor 1006 is positioned at a third location in the housing 926 for sensing when the bar 918 is fully extended from the housing 926 (e.g., the foot support surface 908 is at a maximum possible dorsiflexion angle to the leg support surface 904).

As shown in FIG. 10B, the bar 918 is located at a partially extended position so that some, but not all sensors are activated, allowing determination of applied dorsiflexion angle regardless of whether contact with the dorsiflexion stop 928 on the dorsiflexion limiter 902 was achieved. Note that it is also possible to have zero sensors activated, depending on the level of dorsiflexion applied and the number of sensing elements used. The number and placement of sensing elements determine the resolution of the dorsiflexion angle measurement.

A micro-controller 1008 is wired or wirelessly coupled to the sensors 1002-1006 for sensing a location of the bar 918 within the housing 926 and for logging patient compliance with the stretching program. For example, patient compliance parameters logged by the micro-controller 1008 include a sensed dorsiflexion angle maintained by the splint 900 during a stretching session, whether the sensed dorsiflexion angle is equal to the prescribed dorsiflexion angle, how frequent the splint 900 is used for stretching sessions and for how long each stretching session lasts. Other patient compliance parameters may be sensed or logged by the micro-controller 1008, such as a date and time of a stretching session.

Upon returning to a clinic, the logs from the micro-controller 1008 may be provided to the remote readout/control devices 224a, 224b for evaluation and modification of the stretching program prescribed to a patient. A clinician may recommend a prescriptive change in dorsiflexion angle when the patient is ready to progress to a greater stretch treatment or larger dorsiflexion angle according to clinical assessment or feedback from sensing devices attached to a clinical evaluation splint. This may occur after an initial treatment period of stretching using a lower setting.

Accordingly, the app of diagnostic/tracking software on the control devices 224a, 224b enables a clinician to review past data entries, monitor recordings in real time, as well as download data obtained from a smart home splint 900, if prescribed. If the Home splint 900 version is not outfitted with sensors for monitoring or compliance data, the clinician may use the app to manually document patient self-reported use information. The app also allows the clinician to track past prescriptions for stretching treatment, enter new prescriptions, and track other relevant programs and variables the patient may participate in, such as new or changed diagnoses, physical therapy, supervised exercise, self-reported exercise, or other biometric measurements which inform the use and prescription of stretching treatments. The stretching treatments themselves are also tracked, such as dorsiflexion angle prescribed (or actual angle achieved, which may be different for compliance-monitored patients), duration of total treatment (weeks treated), frequency of treatment sessions, and timing of treatment sessions (i.e., how long the splint is applied for each session).

Figure 11:
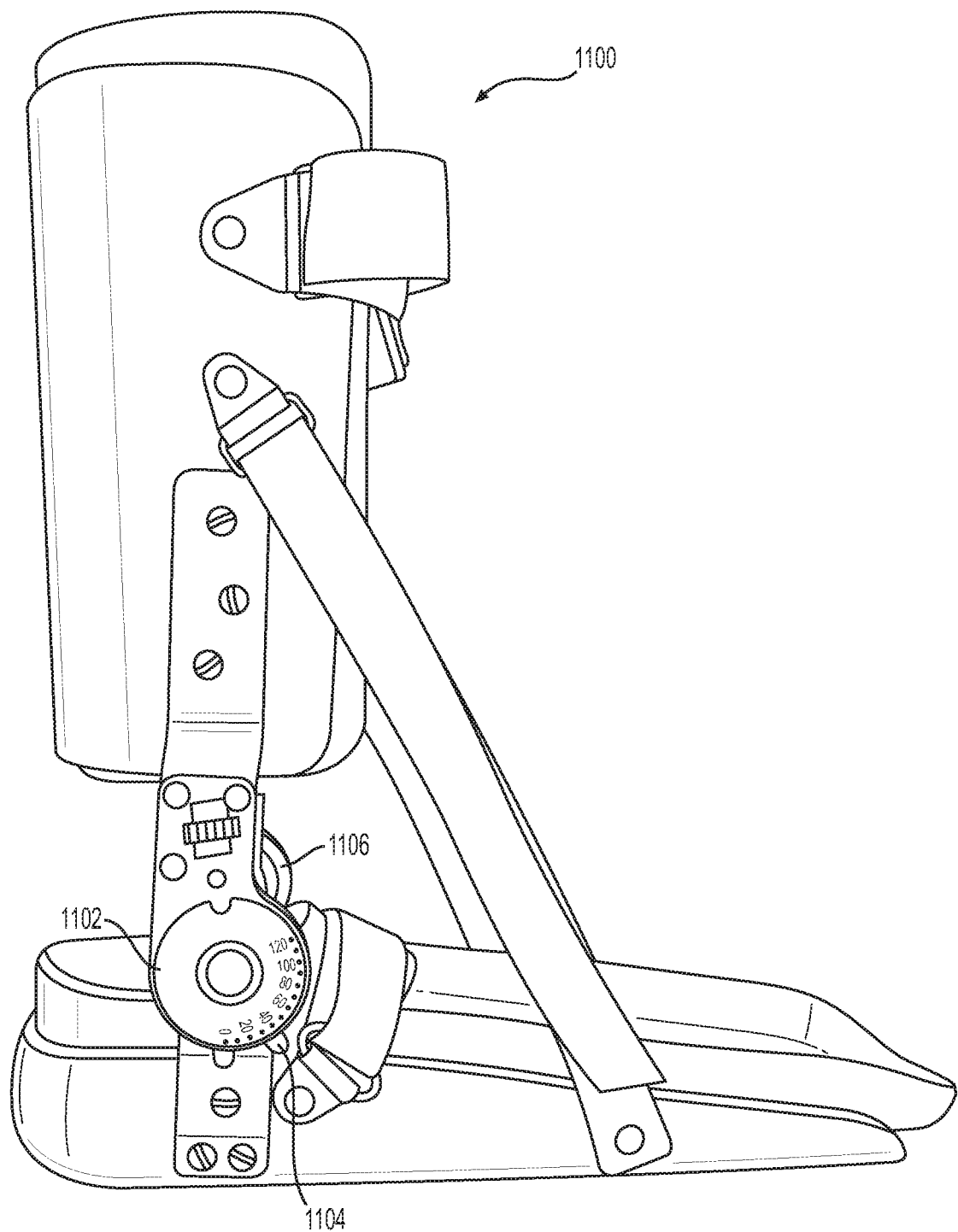
FIG. 11 illustrates an anterior-entry therapeutic splint with a goniometer hinge.

FIG. 11 illustrates an anterior-entry therapeutic splint 1100 with a goniometer hinge 1102. The splint 1100 is substantially the same as the splint 900 with the hinge 910 and dorsiflexion limiter 902 replaced with the goniometer hinge 1102. The goniometer hinge 1102 couples the foot support surface 908 to the leg support surface 904 on a first side. A second goniometer hinge 1106 couples the foot support surface 908 to the leg support surface 904 on a second side, opposite to the first side. The first side may be located along one of the medial or lateral side of a patient's ankle and the second side is located along the other of the medial or lateral side of a patient's ankle. The goniometer hinge 1102 comprises a mechanical stop 1104 for setting the maximum dorsiflexion angle. The mechanical stop 1104 may be configured and locked in place at a clinic based on a prescribed stretching program.

As with the splint 900, one or more sensors may be coupled to the goniometer hinge 1102 and/or goniometer hinge 1106 to measure patient compliance. The angle may be measured by markings on the splint 1100, markings on the hinge, markings on the goniometer 1102, 1106, or measured via sensing mechanism with numerical display on a screen (not shown). The screen may be small and attached to the splint 1100 or the splint angle may be sent to a microcontroller for wireless transmission to a computer or mobile device for display within an app.

Figure 12:
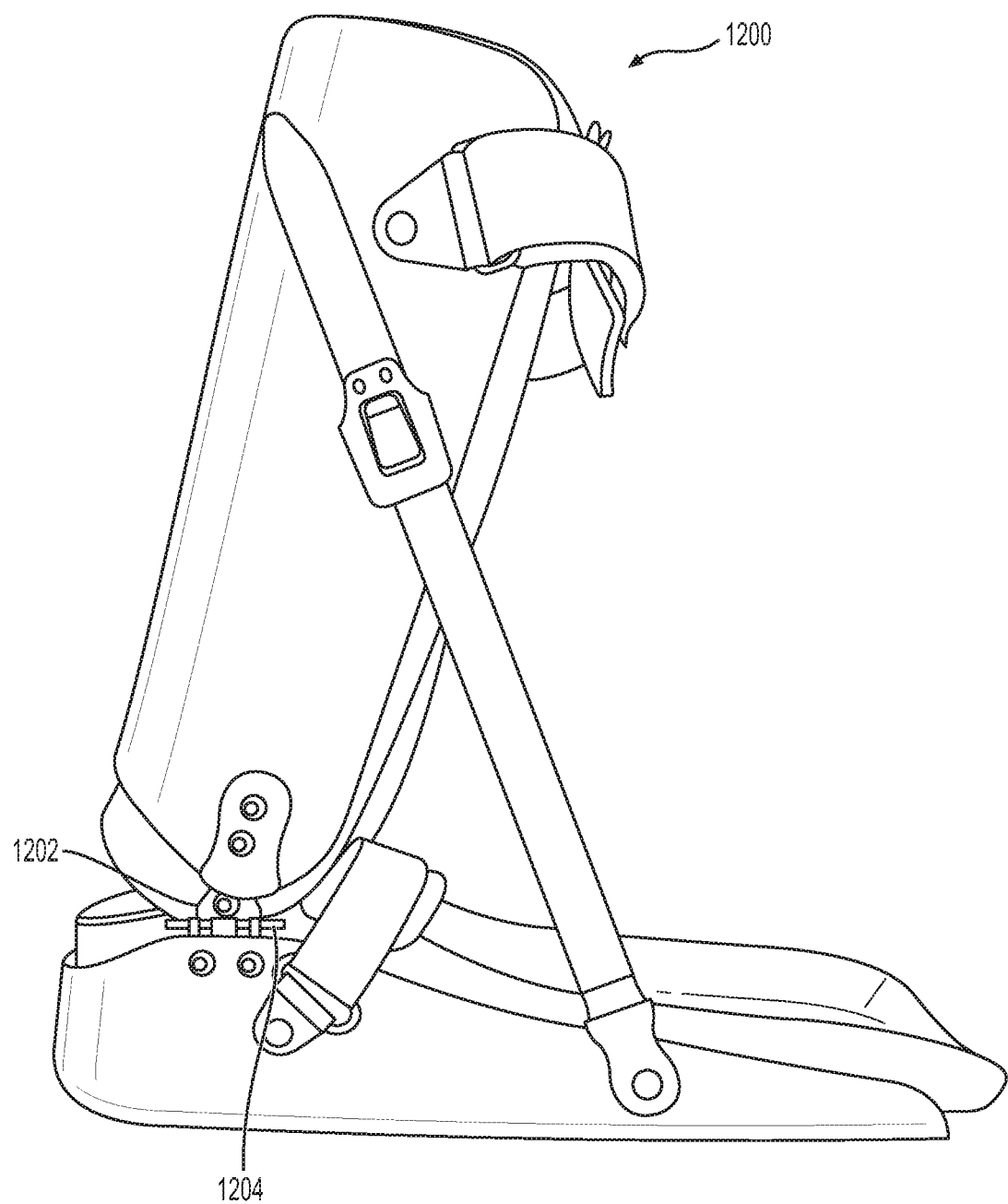
FIG. 12 illustrates an anterior-entry therapeutic splint with a set screw hinge.

FIG. 12 illustrates an anterior-entry therapeutic splint 1200 with a set screw hinge 1202. The splint 1200 is substantially the same as the splint 900 with the hinge 910 and dorsiflexion limiter 902 replaced with the set screw hinge 1202. A set screw 1204 limits a maximum dorsiflexion angle achieved by the splint 1200. The set screw 1204 may be configured and locked in place at a clinic based on a prescribed stretching program. As with the splint 900, one or more sensors may be coupled to the set screw hinge 1202 to measure patient compliance.

Figure 13A:
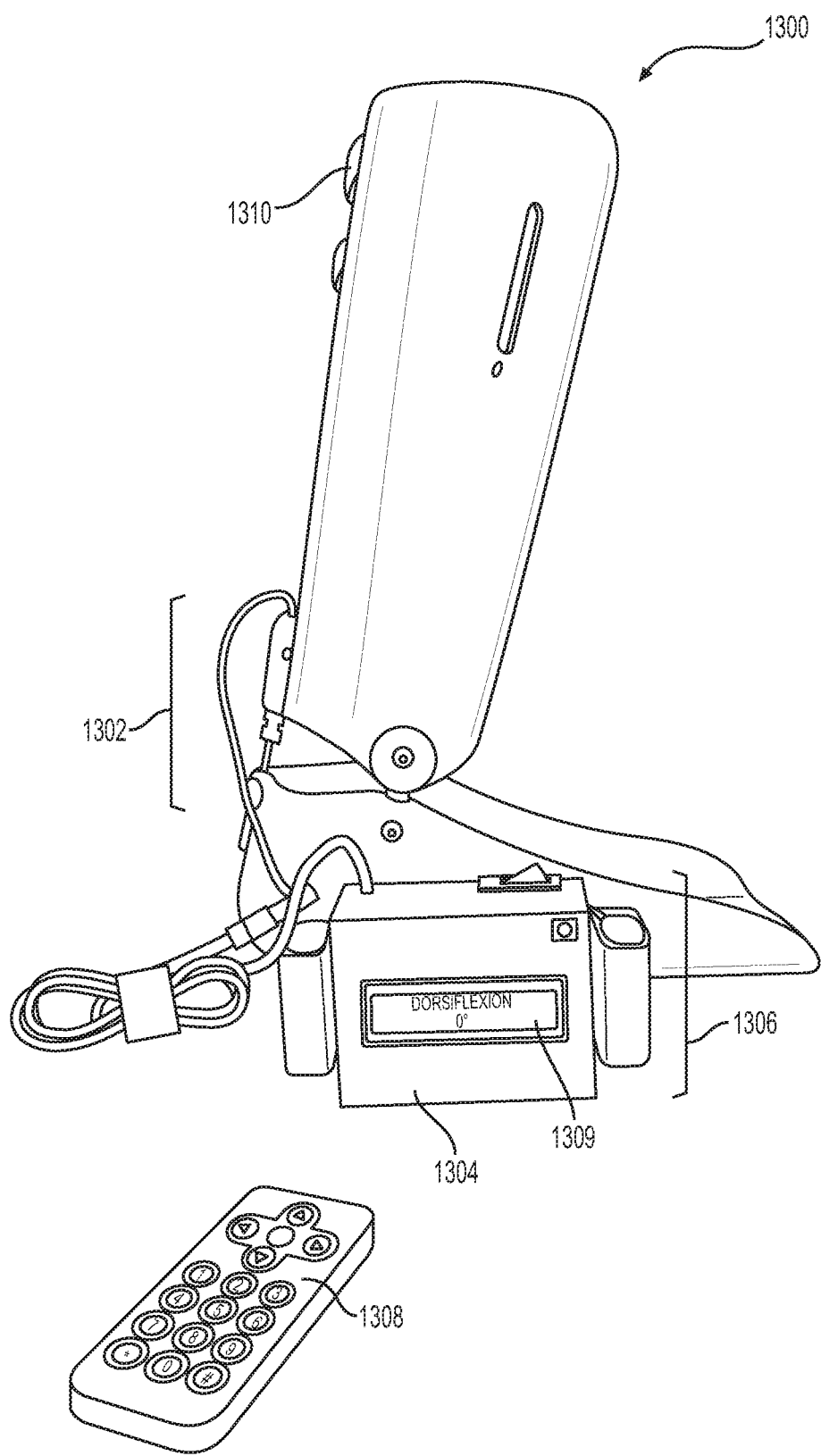
FIGS. 13A-13C illustrate a motorized anterior-entry therapeutic splint.
Figure 13B:
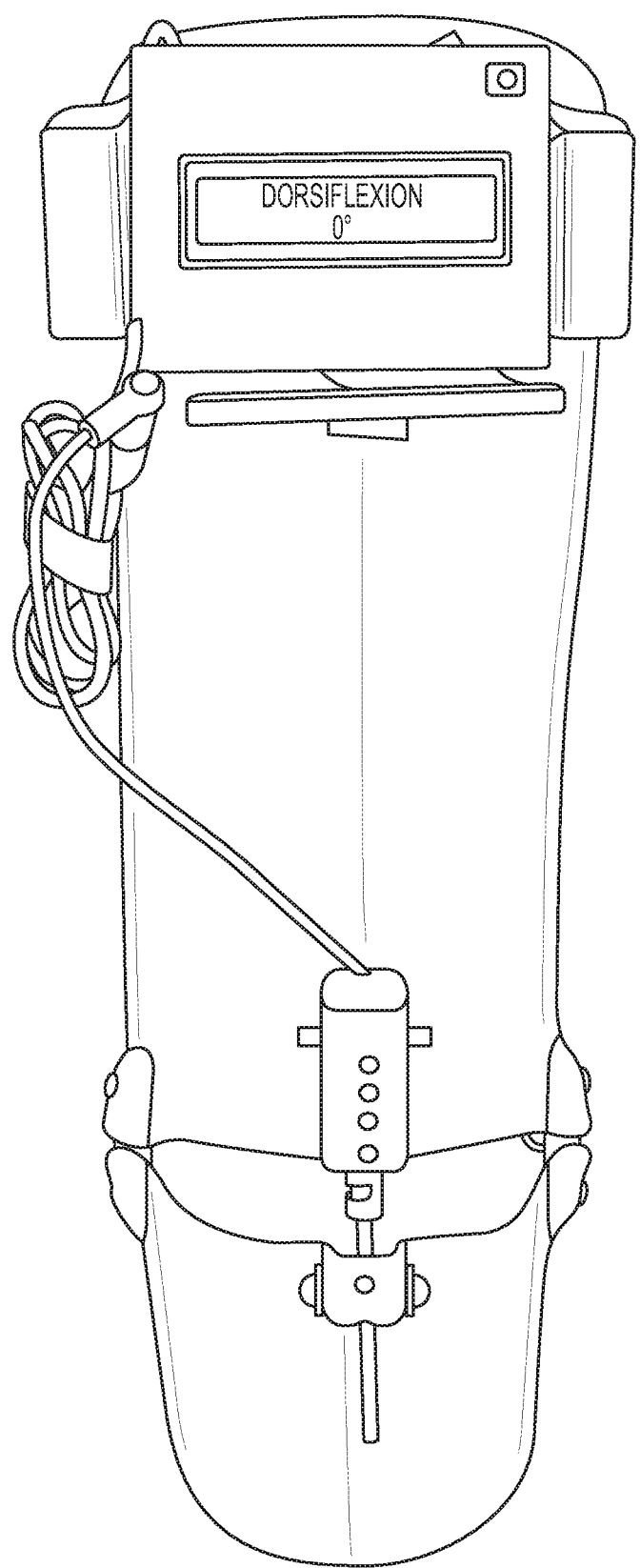
Figure 13C:
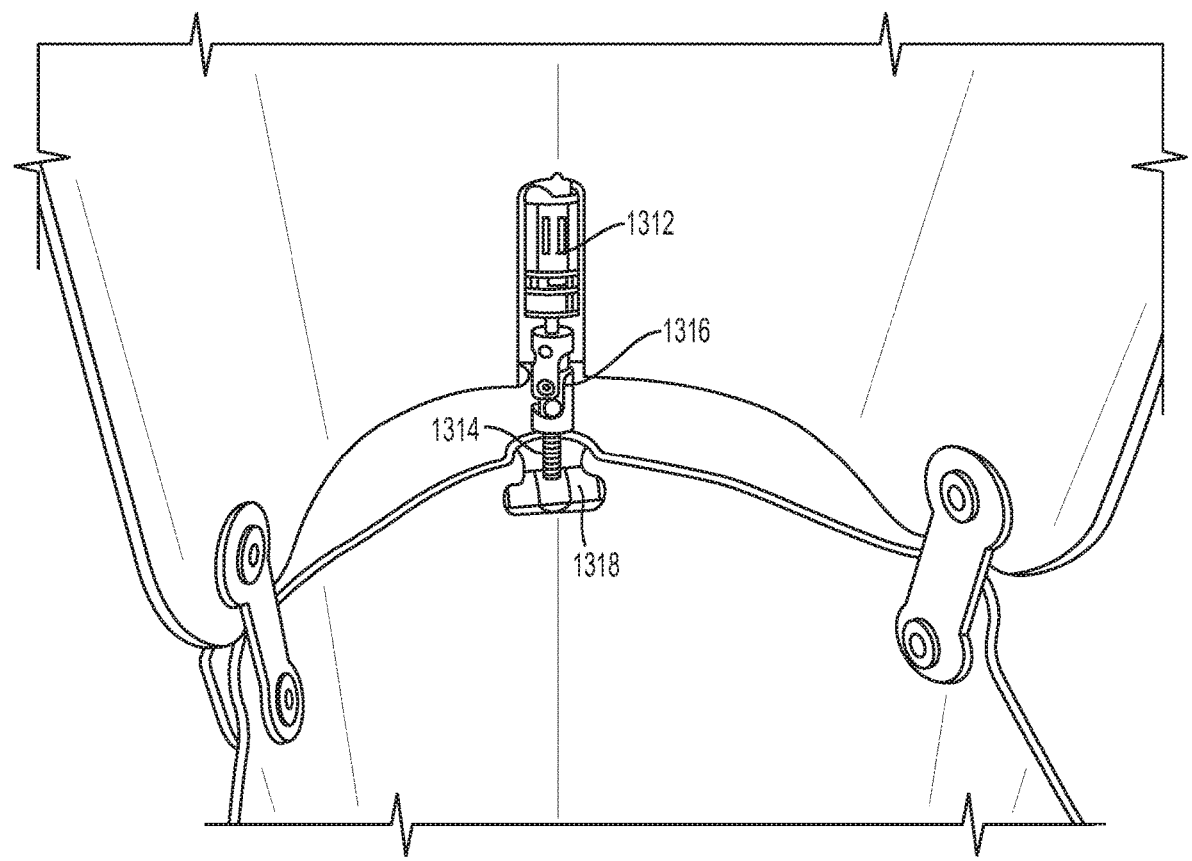

FIGS. 13A-13C illustrate a motorized anterior-entry therapeutic splint 1300. The motorized splint 1300 facilitates automation of application of dorsiflexion through a motorized dorsiflexion limiter 1302. The motorized dorsiflexion limiter 1302 may be located on the splint 1300 at a similar location to the dorsiflexion limiter 902. Other locations for the motorized dorsiflexion limiter 1302 may be used, such as placed near the ankle, built into the hinge, or placed under the foot support surface 908 to push the toe region towards the leg support surface 904.

A control unit 1304 is wired or wirelessly coupled to the motorized dorsiflexion limiter 1302 for control thereof. The control unit 1304 may comprise one or more buttons on the control unit 1304 or on a remote control 1308 for controlling activation of the motorized dorsiflexion limiter 1302 to apply or release dorsiflexion. When a button on the control unit 1304 or remote control 1308 is pushed, a signal is sent from the control unit 1304 to the motorized dorsiflexion limiter 1302 to increase or decrease an applied dorsiflexion angle depending on a current state of the splint 1300 (e.g., dorsiflexion applied or released). Upon reaching a maximum or minimum dorsiflexion angle, the control unit 1304 stops the motorized dorsiflexion limiter 1302. The maximum dorsiflexion angle may be programmed into the control unit 1304 at a clinic based on a prescribed stretching program. One or more batteries 1306 may be provided with the control unit 1304 for supplying power to the control unit 1304 and the motorized dorsiflexion limiter 1302. A display 1309 may show a current dorsiflexion angle of the splint 1300. The splint may additionally include a control unit mount 1310 for mounting the control unit 1304 to the leg support surface 904 of the splint 1300, as shown in FIG. 13B. As with the splint 900, the control unit 1304 may log patient compliance parameters.

As shown in FIG. 13C, the motorized dorsiflexion limiter 1302 comprises a motor 1312. The motor 1312 may be a servo motor or stepper motor in some implementations. The control unit 1304 may be programmed to control the dorsiflexion angle by controlling the motor 1312 through activation by a number of steps, number of rotations, or rotation time, depending on motor design selected or activation of mechanical stops that impede the splint from dorsiflexing farther than desired. Likewise, plantar flexion may be achieved when the motor 1312 is reversed.

The motor 1312 is coupled to a screw 1314 via a coupling 1316 such that activation of the motor 1312 causes the screw 1314 to be rotated. The screw 1314 in turn is coupled to a threaded guide 1318. In the example shown in FIGS. 13A-13C, the threaded guide 1318 is affixed to the foot supporting surface 908, such as on the heel cup. The motor 1312 is affixed to the leg supporting surface 904 and the screw 1314 and coupling 1316 extend therebetween. In some implementations, the location of the threaded guide 1318 and the motor 1312 may be reversed.

Figure 14:
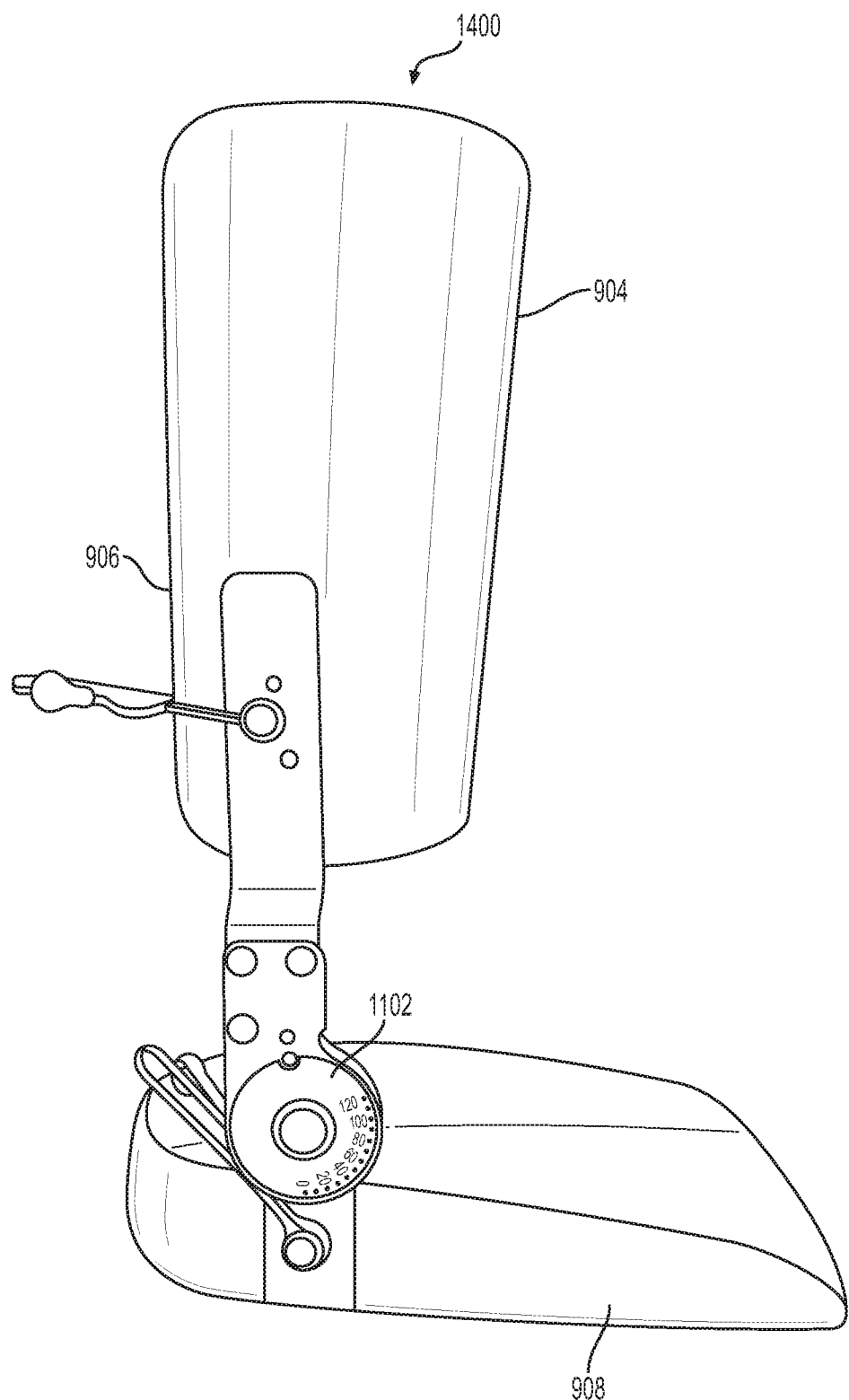
FIG. 14 illustrates a posterior-entry therapeutic splint with a goniometer hinge.

FIG. 14 illustrates a posterior-entry therapeutic splint 1400 with the goniometer hinge 1102. The splint 1400 is substantially the same as the splint 900, but the cavity 906 for the leg supporting surface 904 faces in the opposite direction to facilitate posterior entry into the splint 1400. A posterior entry splint is easier to use for frail patients, and maintains good skin contact for sensors on the posterior side of the calf if housed in a flexible sleeve or strap. The leg supporting surface 904 may have a rigid piece on the anterior of the calf and open or soft posterior side where a strap secures the back of the calf in place. The foot supporting surface 908 may include heel cup or may have an open heel design so the foot may slide in easily.

Additionally, the posterior entry splint 1400 may be used in conjunction with a ratcheting hinge. In operation, a patient's leg enters the splint 1400 posteriorly and then the subject leans forward to induce the desired level of dorsiflexion from a seated or semi-seated position.

While a particular implementation of the anterior entry splint 1400 is described above, any of the above embodiments may be configured for anterior entry similar to the splint 1400.

If plantar support and plantar sensing is not required for the splint 1400, the splint 1400 configuration can be completely anterior, e.g. along the front of the calf and along the top of the foot for posterior entry of the leg. This is advantageous for a ratcheting hinge design that asks the user to lean into the desired level of dorsiflexion prior to extending the knee for the treatment session.

In this implementation, the foot supporting surface 908 rests upon and makes contact with a dorsal portion a patient's foot. The foot supporting surface 908 may have one or more contours for conforming to a shape of the dorsal portion of the patient's foot and ankle. One or more straps may extend from the foot supporting surface 908 around a plantar portion of the patient's foot for securely maintaining contact between the foot supporting surface 908 and the dorsal portion of the patient's foot. A dorsiflexion limiter may extend at an angle from a top surface of the foot supporting surface 908 to the leg supporting surface 904. Other variations and configurations are contemplated consistent with the teachings of the pending disclosure.

Additive manufacturing presents additional possibilities for vascular splints. This may allow splints to be produced to match the desired dorsiflexion prescription for a specific patient. Additionally, patient-specific body scans can allow customization of a curvature and sizing for optimal fit and addition of sensor insertion locations that may be specific for that patient or patient subgroup. These splints may change simple parameters such as overall size and curvature of an existing design, or may utilize geometric information about the entire lower leg to create a new, fully conformed custom splint which dorsiflexes to the prescribed level. Hinges for additive manufactured splints may be added post-printing, produced separately via additive manufacturing methods and then assembled (such as in FIGS. 15A-15B), or produced fully assembled in a single run (FIG. 16).

Figure 15A:
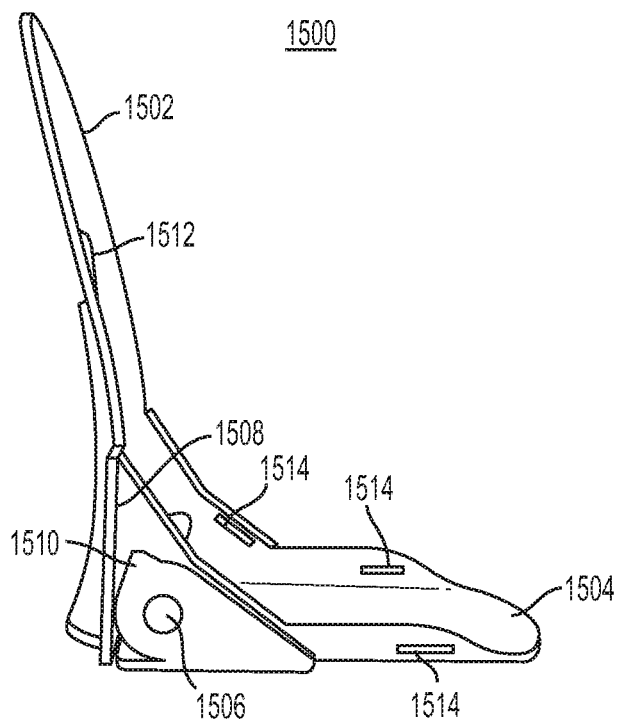
FIGS. 15A and 15B illustrate an additive manufactured therapeutic splint with an assembled hinge.
Figure 15B:
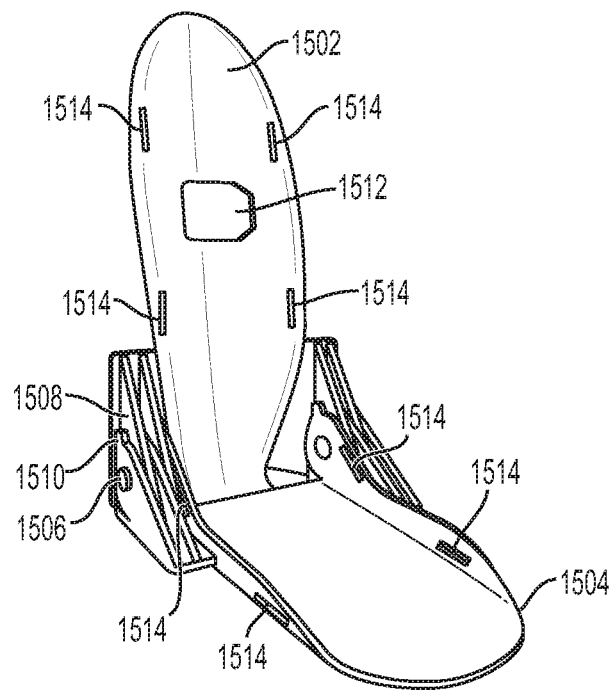

FIGS. 15A and 15B illustrate an additive manufactured therapeutic splint 1500 with an assembled hinge 1506. The splint 1500 comprises separately additive manufactured leg supporting surface 1502 and foot supporting surface 1504. A hinge 1506 may be added or produced separately via additive manufacturing and assembled with the leg supporting surface 1502 and foot supporting surface 1504 to construct the splint 1500. The dorsiflexion angle is established by a cam surface 1508 on the leg supporting surface 1502 and a cam block 1510 on the foot supporting surface 1504. Upon rotation of the leg supporting surface 1502 and foot supporting surface 1504 to the prescribed dorsiflexion angle the cam block 1510 interferes with the cam surface 1508 and prevents further relative rotation therebetween. A sensor window 1512 provides for insertion of near-infrared spectroscopy or other sensing devices for use with the splint 1500. The splint 1500 also comprises a plurality of strap slots 1514 for providing one or more of a foot strap, ankle strap, and one or more leg straps.

Figure 16:
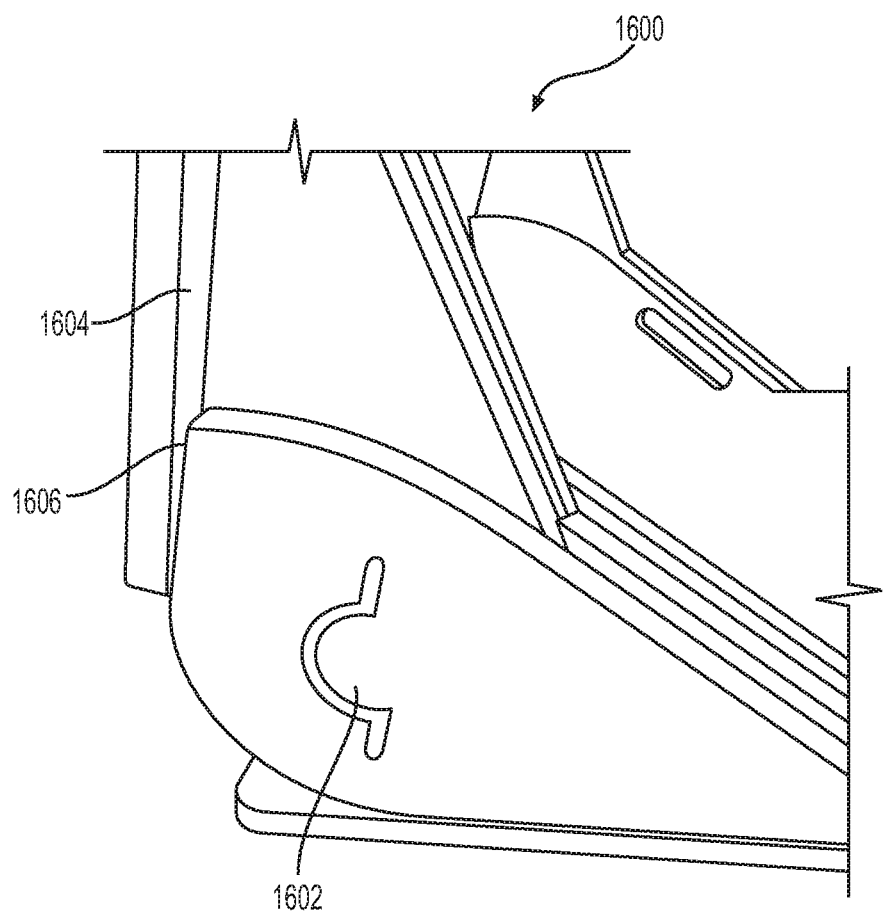
FIG. 16 illustrates an additive manufactured therapeutic splint with an integrated hinge.

FIG. 16 illustrates an additive manufactured therapeutic splint 1600 with an integrated hinge 1602. The splint 1600 is constructed substantially similar to the splint 1500 apart from the integrated hinge 1602. The splint 1600 comprises a cam surface 1604 and a cam block 1606 for setting the maximum dorsiflexion angle. This splint 1600 was produced without support material, and may also be produced with secondary material for hinge spacing.

Other embodiments of mechanisms for setting the desired dorsiflexion angle are contemplated by this disclosure. For example a tension-based control of dorsiflexion splinting is contemplated. With such devices a stainless steel wire is threaded through a system of guides and an adjustment knob allows a mechanical advantage (e.g., 4:1) when tightening the knob.

The various embodiments described above are provided by way of illustration only and should not be construed to limit the scope of the present disclosure. Those skilled in the art will readily recognize that various modifications and changes may be made to the present disclosure without following the example embodiments and implementations illustrated and described herein, and without departing from the spirit and scope of the disclosure and claims here appended and those which may be filed in non-provisional patent application(s). Therefore, other modifications or embodiments as may be suggested by the teachings herein are particularly reserved.

What is claimed is:

1. A splint system for diagnostic and/or therapeutic functions for a patient with a vascular impairment, comprising:
   a splint having:
      a leg supporting portion and a foot supporting portion, that are configured to support and secure the leg and foot of the patient;
      a locally and/or remotely controllable portion for setting a dorsiflexion angle of the foot of the patient, including electrical and/or mechanical controls and one or more actuators for setting of the dorsiflexion angle, for providing treatment to improve vascular function; and
      one or more physiological parameter sensors for measuring one or more physiological parameters of the leg and/or foot of the patient, wherein the one or more physiological parameters are associated with vascular function in the leg and/or foot of the patient, wherein the physiological parameters comprises tissue oxygenation of one or more plantar flexor muscles of the leg of the patient; and
   a controller configured to receive the measurement of the tissue oxygenation of the one or more plantar flexor muscles of the leg of the patient and facilitate determination of a prescription dorsiflexion angle that decrease muscle oxygenation by an effective amount.

2. The splint system of claim 1, wherein the vascular impairment is peripheral arterial disease (PAD).

3. The splint system of claim 1, wherein the treatment to improve the vascular function comprises improving blood flow and/or oxygenation.

4. The splint system of claim 1, wherein setting a dorsiflexion angle of the foot of the patient comprises holding the foot at a predetermined dorsiflexion angle using a plate that is located at the foot supporting portion of the splint and is operatively coupled to the one or more actuators.

5. The splint system of claim 1, wherein the leg supporting portion extends behind the knee of the patient to prevent bending of the knee during use of the splint.

6. The splint system of claim 1, wherein the sensors comprise one or more sensors for measuring tension applied by the splint to the leg and/or foot.

7. The splint system of claim 6, wherein the splint further comprises one or more components for preventing the tension applied by the splint to reach or exceed a level associated with a clinically undesirable result.

8. The splint system of claim 1, wherein the physiological parameters comprise one or more of:
   oxygen saturation;
   pulse;
   blood pressure;
   ankle-brachial index;
   pulse wave velocity;
   femoral bruit;
   skin temperature; or
   blood flow velocity.

9. The splint system of claim 1, wherein the sensors comprise one or more of:
   at least one blood pressure cuff;
   at least one bruit sensor;
   at least one dorsiflexion angle sensor;
   at least one near infrared spectroscopy contact point;
   at least one doppler ultrasound device or tonometer;
   at least one photoplethysmogram;
   at least one tensiometer;
   at least one plantar pressure measurement sensor;
   at least one dorsalis pedis sensor; or
   at least one skin temperature sensor.

10. The splint system of claim 1, wherein the system further comprises one or more sensors disposed separately from the splint, and wherein the sensors of the splint and/or the one or more sensors disposed separately comprise at least one of:
   a brachial cuff;
   an ankle cuff; or
   a blood pressor cuff integrated with the splint.

11. The splint system of claim 1, wherein the system further comprises one or more computing devices coupled via wired and/or wireless connections to the splint, configured for displaying visual representations of the measured physiological parameters and/or entry of data associated with the measured physiological parameters.

12. The splint system of claim 1, wherein the system further comprises a remote control device configured to remotely control the dorsiflexion angle.

13. The splint system of claim 1, wherein the sensors comprise a perfusion magnetic resonance imaging (MRI) or a blood oxygen level dependent (BOLD) MRI.

14. The splint system of claim 1, wherein the sensors comprise a near-infrared spectroscopy (NIRS) sensor configured to measure the tissue oxygenation of the one or more plantar flexor muscles of the leg of the patient.

15. The splint system of claim 14, wherein the NIRS is further configured to measure oxyhemoglobin (O2Hb), deoxyhemoglobin (HHb), and/or total tissue hemo(+myo) globin (tHb).

16. The splint system of claim 14, wherein the NIRS sensor uses a light source with two or more wavelengths of light and two detectors placed at different distances from the light source.

17. The splint system of claim 1, wherein the effective amount induces local ischemia in the one or more plantar flexor muscles of the leg of the patient.

18. The splint system of claim 17, wherein the effective amount is sufficient to treat peripheral artery disease (PAD).

19. The splint system of claim 17, wherein the effective amount is a muscle oxygenation of less than 50%.

20. The splint system of claim 19, wherein the effective amount is a muscle oxygenation of between 40-50%.

21. The splint system of claim 17, wherein the effective amount is a decrease in a baseline oxygenation level of between 30-40%.

22. The splint system of claim 17, wherein the controller is configured to facilitate determination of the dorsiflexion angle that decrease muscle oxygenation by an effective amount upon setting the dorsiflexion angle of the foot of the patient at each of a plurality of regular dorsiflexion angle increments.

23. The splint system of claim 22, wherein the plurality of regular dorsiflexion angle increments are at 1-5° increments.

24. The splint system of claim 17, wherein the controller is configured to display the measurement of the tissue oxygenation of the one or more plantar flexor muscles of the leg of the patient and receive an input for setting the dorsiflexion angle of the foot of the patient.

25. The splint system of claim 17, wherein the controller is configured to receive the measurement of the tissue oxygenation of the one or more plantar flexor muscles of the leg of the patient and automatically setting the dorsiflexion angle of the foot of the patient.

* * * * *